(12) United States Patent
Schaub et al.

(10) Patent No.: US 10,138,196 B2
(45) Date of Patent: Nov. 27, 2018

(54) PROCESS FOR PREPARING AN UNSATURATED CARBOXYLIC ACID SALT

(71) Applicant: BASF SE, Ludwigshafen (DE)

(72) Inventors: Thomas Schaub, Neustadt (DE); Nuria Huguet Subiela, Heidelberg (DE); Rocco Paciello, Bad Duerkheim (DE); Donata Maria Fries, Mannheim (DE); Simone Manzini, Certosa di Pavia (IT)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 15/573,276

(22) PCT Filed: May 9, 2016

(86) PCT No.: PCT/EP2016/060328
§ 371 (c)(1),
(2) Date: Nov. 10, 2017

(87) PCT Pub. No.: WO2016/180775
PCT Pub. Date: Nov. 17, 2016

(65) Prior Publication Data
US 2018/0134646 A1    May 17, 2018

(30) Foreign Application Priority Data
May 13, 2015 (EP) ..................... 15167626

(51) Int. Cl.
C07C 51/15    (2006.01)
C07C 51/48    (2006.01)
B01J 31/24    (2006.01)

(52) U.S. Cl.
CPC ............ C07C 51/15 (2013.01); B01J 31/24 (2013.01); C07C 51/48 (2013.01)

(58) Field of Classification Search
CPC ........... C07C 51/15; C07C 51/48; B01J 31/24
See application file for complete search history.

(56) References Cited

U.S. PATENT DOCUMENTS

| | | | |
|---|---|---|---|
| 4,792,620 A * | 12/1988 | Paulik ............... | B01J 31/0231 560/232 |
| 6,437,198 B1 * | 8/2002 | Friedrich ............. | B01J 19/18 568/851 |
| 2011/0218359 A1 | 9/2011 | Limbach et al. | |

FOREIGN PATENT DOCUMENTS

| WO | WO 2013/098772 A1 | 7/2013 | |
|---|---|---|---|
| WO | WO-2013098772 A1 * | 7/2013 | ............. C07B 41/08 |

OTHER PUBLICATIONS

Norskov et al, Nature Chemistry, Towards the Computational Design of Solid Catalysts, 2009, 1, pp. 37-46. (Year: 2009).*
Doherty et al, Journal of Organometallic Chemistry, Selectivity for Methoxycarbonylation of Ethylene Versus CO-Ethylene Copolymerization with Catalysts Based on C4-bridged Bidentate Phosphines and Phospholes, 2001,640, pp. 182-196. (Year: 2001).*
International Search Report and Written Opinion of the International Searching Authority dated Jun. 16, 2016 in PCT/EP2016/060328 filed May 9, 2016.
International Preliminary Report on Patentability dated Nov. 14, 2017 in PCT/EP2016/060328 filed May 9, 2016.
Michael L Lejkowski, et al., "The First Catalytic Synthesis of an Acrylate from $CO_2$ and an Alkene—A Rational Approach" Chemistry—A European Journal, vol. 18, 2012, pp. 14017-14025.
Núria Huguet, et al., "Nickel-Catalyzed Direct Carboxylation of Olefins with $CO_2$: One-Pot Synthesis of α,β-Unsaturated Carboxylic Acid Salts" Chemistry—A European Journal, vol. 20, No. 51, XP055203743, Dec. 15, 2014, pp. 16858-16862.
U.S. Appl. No. 15/311,012, filed Aug. 3, 2017, 2017/0217869, Limbach et al., Aug. 2017.
U.S. Pat. No. 9,758,461, Sep. 12, 2017, 2017/0107166, Limbach et al., Apr. 2017.

* cited by examiner

*Primary Examiner* — Paul A Zucker
(74) *Attorney, Agent, or Firm* — Oblon, McClelland, Maier & Neustadt, L.L.P.

(57) ABSTRACT

A catalytic process for preparing an α,β-ethylenically unsaturated carboxylic acid salt from an alkene, carbon dioxide and an alkoxide having a secondary or tertiary carbon atom directly bound to a [O⁻] group is described. The alcohol byproduct is distilled off after an intermediate phase separation. This provides pure β,β-ethylenically unsaturated carboxylic acid salt at minimum effort.

17 Claims, No Drawings

PROCESS FOR PREPARING AN UNSATURATED CARBOXYLIC ACID SALT

The present invention relates to a catalytic process for preparing an α,β-ethylenically unsaturated carboxylic acid salt from an alkene, carbon dioxide, and an alkoxide. The alcohol byproduct (the conjugate acid of the alkoxide) is distilled off after an intermediate phase separation step. α,β-ethylenically unsaturated carboxylic acids, in particular acrylic acid and derivatives thereof are important industrial chemicals and monomer units for producing water-absorbing resins, i.e. superabsorbents.

The direct addition of $CO_2$ onto ethene to give acrylic acid is industrially unattractive due to thermodynamic limitations ($\Delta G$=42.7 kJ/mol at 298 K) and the unfavorable equilibrium, which at room temperature is virtually completely to the side of the reactants ($K_{298}$=7×10$^{-7}$). On the other hand, the formation of sodium acrylate and water from $CO_2$, ethene and sodium hydroxide is thermodynamically favored ($\Delta G$=−56.2 kJ/mol at 298 K, $K_{298}$=7.1×10$^9$). However, the nucleophilic base sodium hydroxide is immediately reacting with $CO_2$ to form sodium carbonate or sodium bicarbonate. Even if less nucleophilic bases are used, the acrylate formation is kinetically inhibited and therefore requires a homogeneous or heterogeneous carboxylation catalyst.

Limbach et al. (WO 2013/098772, Chem. Eur. J. 2012, 18, 14017-14025) described a catalytic process for preparing an alkali metal or alkaline earth metal salt of an α,β-ethylenically unsaturated carboxylic acid, wherein a) a transition metal-alkene complex is reacted with $CO_2$ to give a metallalactone, b) the metallalactone is reacted with a base to give an adduct of the alkali metal or alkaline earth metal salt of the α,β-ethylenically unsaturated carboxylic acid with the transition metal complex, the base being selected from alkali metal or alkaline earth metal hydroxides and alkali metal or alkaline earth metal superbases, and c) the adduct is reacted with an alkene to release the alkali metal or alkaline earth metal salt of the α,β-ethylenically unsaturated carboxylic acid and regenerate the transition metal-alkene complex. In step c), the transition metal-alkene complex is regenerated and is available again for step a). This completes the catalytic cycle. According to the teaching of WO 2013/098772, the base is added separately from the addition of the $CO_2$ in order to prevent a direct reaction of the base with the $CO_2$. In other words, the process requires separation of the times and/or sites of addition of the alkene and $CO_2$ reactants on the one hand and the base reactant on the other hand (page 16 of WO 2013/098772). Dividing the catalytic cycle into two halves: a $CO_2$-rich regime, and a $CO_2$-poor regime is also suggested in Chem. Eur. J. 2012, 18, 14017-14025. As stated at page 14021, it is avoided to expose the reaction mixture to both, alkoxides and carbon dioxide at the same time. It is presumed that the alkoxides would irreversibly form fairly stable carbonic acid half esters with $CO_2$. Accordingly, sodium acrylate was obtained in WO 2013/098772 at an overall yield of 1020% (2.55 mmol) based on the Nickel (0.25 mmol) only after 18 cycles of subsequent treatment of the reaction mixture with $CO_2$ (in a first step) and then with NaOtBu (in a second step). Such a process requires considerable effort, in particular in terms of energy and time, because each cycle includes increasing and decreasing $CO_2$ partial pressure, increasing and decreasing ethene partial pressure, and adding NaOtBu at decreased gas pressure.

Recently, Huguet et al. have described the direct nickel-catalyzed carboxylation of alkenes with $CO_2$ in the presence of sodium phenoxide, specific fluorine substituted sodium phenoxides or methyl substituted sodium phenoxides (Chem. Eur. J. 2014, 20, 16858-16862). Catalytic turnover was achieved under simultaneous presence of high $CO_2$ partial pressure and phenoxide base. Maximum turnover was achieved with fluorine substituted sodium phenoxides, in particular with sodium 2-fluoro phenoxide or sodium 3-fluoro phenoxide using nickel complexes comprising structurally constrained bidentate P,P ligands, such as BINAPINE, TangPhos, DuanPhos, or BenzP*. In these P,P ligands, the atoms bridging the phosphorous atoms are part of cyclic substructures.

It is difficult to carry out the nickel-catalyzed carboxylation described in Chem. Eur. J. 2014, 20, 16858-16862 on an industrial scale. The ligands that are favorable in terms of turnover are expensive and organofluorine compounds (e.g. fluoro substituted phenoxide bases) are potentially harmful pollutants even when only small amounts are emitted from production sites. Carrying out this nickel-catalyzed carboxylation on an industrial scale would thus require substantial effort for avoiding any emission of ligand or base. It is also difficult to separate the main α,β-ethylenically unsaturated carboxylic acid salt product from the phenolic byproduct because both possess similar solubility in polar and apolar solvents.

The problem of the present invention is thus the provision of a more efficient catalytic process for preparing α,β-ethylenically unsaturated carboxylic acid derivatives from $CO_2$ and an alkene, in particular to overcome the risk of emitting potentially harmful compounds and to avoid any additional effort for obtaining a sufficiently pure α,β-ethylenically unsaturated carboxylic acid salt.

The problem is solved by a catalytic process for preparing an α,β-ethylenically unsaturated carboxylic acid salt, wherein
  a) an alkene and carbon dioxide are contacted with a carboxylation catalyst and an alkoxide, the alkoxide having a secondary or tertiary carbon atom directly bound to a [O⁻] group, to obtain a crude reaction product comprising the α,β-ethylenically unsaturated carboxylic acid salt and an alcohol byproduct which is the conjugate acid of the alkoxide,
  b) at least part of the crude reaction product is contacted with a polar solvent such that a first liquid phase in which the α,β-ethylenically unsaturated carboxylic acid salt is enriched, and a second liquid phase in which the carboxylation catalyst is enriched, are obtained, and
  c) an alcohol byproduct is distilled off from the first liquid phase.

The process according to the invention is efficient. A catalytic turnover, i.e. the provision of the α,β-ethylenically unsaturated carboxylic acid salt at molar excess based on the transition metal, is achieved in step a) at minimum effort in a single stage without increasing and decreasing the $CO_2$ partial pressure in multiple subsequent reaction cycles as required in the process of WO 2013/098772 and Chem. Eur. J. 2012, 18, 14017-14025.

This is surprising because until now it was assumed that all alkoxides would irreversibly form fairly stable carbonic acid half esters with $CO_2$ and that the formation of these half esters would prevent a catalytic turnover in a single stage. It has now been found that catalytic turnover is achieved with the alkoxide having a secondary or tertiary carbon atom directly bound to the [O⁻] group even in the presence of high partial pressure of $CO_2$. There is thus no need of adding the alkoxide separately from $CO_2$ by increasing and decreasing the $CO_2$ partial pressure in step a), as required in 2013/098772.

The partial pressure of carbon dioxide in step a) is thus preferably maintained above 1 bar. It is, for example, maintained at at least 2 bar, in particular at at least 4 bar, most preferably at at least 6 bar. The partial pressure of carbon dioxide in step a) is preferably maintained below 200 bar. It is, for example, maintained at at most 160 bar, in particular at at most 140 bar, most preferably at at most 120 bar. In step a) of the process according to the invention, the partial pressure of carbon dioxide is preferably maintained in a range from 1 to 200 bar, preferably from 2 to 160 bar, in particular from 4 to 140 bar, further preferred from 6 to 120 bar, most preferably from 10 to 100 bar.

There is no more risk of emitting potentially harmful pollutants such as organofluorine compounds. Any emission of alkoxides having secondary or tertiary carbon atoms directly bound to the [O⁻] group is less harmful than the emission of fluoro substituted phenoxide bases.

Any additional effort for obtaining a sufficiently pure α,β-ethylenically unsaturated carboxylic acid salt is avoided in the process according to the invention. Any byproduct (i.e. alcohol byproduct being the conjugate acid of the alkoxide) is efficiently removed from the first liquid phase by distillation in step c). Additional effort is avoided because the removal of the polar solvent from the first liquid phase would anyhow require a separation step, i.e. a distillation step in which the alcohol byproduct is obtained as a second distillation fraction. On the other hand, the separation of phenols (conjugate acids of phenolate bases as used in prior art processes) requires additional effort. The high boiling point of phenols complicates their separation by means of distillation.

The process according to the invention requires that the alkoxide is an alkoxide having a secondary or tertiary carbon atom directly bound to a [O⁻] group. It is assumed that any undesired direct reaction of the alkoxide with $CO_2$ and in particular the undesired half ester formation is more efficiently suppresses when the residue bound to the [O⁻] group is sterically demanding. In general, tertiary residues are sterically more demanding than secondary residues. The alkoxide is thus preferably tertiary. This means that the alkoxide having a secondary or tertiary carbon atom directly bound to the [O⁻] group is preferably an alkoxide having a tertiary carbon atom directly bound to the [O⁻] group.

The expression "alkoxide having a secondary or tertiary carbon atom directly bound to a [O⁻] group" refers to a compound comprising subunits of the following general formula (I)

$$^-O—R \qquad (I)$$

wherein R is a hydrocarbyl residue which comprises a carbon atom that is bound to the oxygen shown in general formula (I), and
  one hydrogen atom that is bound to this carbon atom and two carbon atoms that are bound to this carbon atom,
  or
  three carbon atoms that are bound to this carbon atom.

Accordingly, the expression "alkoxide having a tertiary carbon atom directly bound to a [O⁻] group" refers to a compound comprising subunits of general formula (I) wherein R is a hydrocarbyl residue which comprises a carbon atom that is bound to the oxygen shown in general formula (I), and three carbon atoms that are bound to this carbon atom.

The hydrocarbyl residue R may be acyclic, cyclic or comprise cyclic substructures. R is preferably acyclic.

The hydrocarbyl residue R may be saturated or unsaturated. Hydrocarbyl residues R that are saturated do only comprise single bonds, whereas hydrocarbyl residues R that are unsaturated do comprise at least one double bond. The hydrocarbyl residue R is preferably saturated.

Any hydrogen atom comprised by R may, for example, be substituted by one or multiple non-interfering substituents. A non-interfering substituent is a substituent that is inert under the conditions of the process according to the invention, i.e. a substituent that does not react with any compound or intermediate being in contact with the alkoxide or with the conjugate acid of the alkoxide in the process according to the invention. Suitable substituents include F, Cl, and O—$C_1$-$C_6$-alkyl. R is preferably unsubstituted which means that R consists of hydrogen and carbon atoms.

In a preferred process according to the invention, the alkoxide is derived from an alcohol that is not decomposed when it is distilled. The alkoxide having a secondary or tertiary carbon atom directly bound to a [O⁻] group is converted into an alcohol byproduct which is the conjugate acid of the alkoxide in step a). This alcohol byproduct is distilled off in step c). The alkoxide may thus be selected based on the decomposition temperature of its conjugate acid, i.e. of the conjugate alcohol. It is generally preferred, when the decomposition temperature of the conjugate acid of the alkoxide is much higher than its boiling temperature at 1 bar. The decomposition temperature of the conjugate acid of the alkoxide is preferably at least 10° C., in particular at least 20° C., for example 30° C. to 200° C. higher than its boiling temperature at 1 bar.

This difference between decomposition temperature and boiling temperature can, for example, be established by choosing the alkoxide based on the molecular weight of its conjugate acid, i.e. of the conjugate alcohol. Low molecular weight compounds tend to have low boiling temperatures. The molecular weight of the conjugate acid of the alkoxide is, for example, at most 200 g/mol, preferably at most 160 g/mol, in particular at most 140 g/mol, most preferably at most 120 g/mol. The molecular weight of the conjugate acid of the alkoxide is, for example, in the range from 59 to 200 g/mol, preferably in the range from 73 to 160 g/mol, in particular in the range from 73 to 140 g/mol, most preferably in the range from 73 to 120 g/mol.

In a preferred process according to the invention, the alkoxide having a secondary or tertiary carbon atom directly bound to a [O⁻] group comprises subunits of the following general formula (II)

$$^-O—CR^1(R^2)_2 \qquad (II)$$

wherein
  $R^1$ is H or $R^2$, and
  each $R^2$ is independently selected from $C_1$-$C_{10}$-hydrocarbyl or any two or three $R^2$ together with the secondary or tertiary carbon atom to which they are bonded are one or multiple 3- to 8-membered carbocycles.

Each $R^2$ is, for example, independently selected from $C_1$-$C_{10}$-alkyl, $C_3$-$C_{10}$-cycloalkyl, and $C_6$-$C_{10}$-aryl.

In a particularly preferred process according to the invention, the alkoxide having a secondary or tertiary carbon atom directly bound to a [O⁻] group comprises subunits selected from ⁻O-tert-butyl, ⁻O-iso-propyl, ⁻O-sec-butyl, ⁻O-cyclopropyl, and ⁻O-((1-methyl)-cyclopropyl), ⁻O-cyclohexyl, and ⁻O-((1-methyl)-cyclohexl)).

A preferred alkoxide having a secondary or tertiary carbon atom directly bound to a [O⁻] group is tert-butoxide.

The alkoxide having a secondary or tertiary carbon atom directly bound to a [O⁻] is, for example, selected from alkali metal alkoxides and alkaline earth metal alkoxides. Alkali metal and in particular sodium alkoxides are preferred.

Particularly preferred alkoxides having a secondary or tertiary carbon atom directly bound to a [O⁻] are sodium tert-butoxide and sodium iso-propoxide. The most preferred alkoxide having a secondary or tertiary carbon atom directly bound to a [O⁻] is sodium tert-butoxide.

The alkoxide can, for example, be added in solid form or as a solution.

A particularly preferred carboxylation catalyst is a transition metal complex.

The term "transition metal complex" used herein comprises, in a generic manner, all transition metal complexes through which the catalytic cycle is supposed to pass, i.e. transition metal-alkene complexes, metallalactones and adducts wherein the α,β-ethylenically unsaturated carboxylic acid salt coordinates to the transition metal.

In general, the transition metal complex comprises, as the active metal, at least one element of groups 4 (preferably Ti, Zr), 6 (preferably Cr, Mo, W), 7 (preferably Re), 8 (preferably Fe, Ru), 9 (preferably Co, Rh) and 10 (preferably Ni, Pd, Pt) of the Periodic Table of the Elements. Preference is given to nickel and palladium. Most preferably, the transition metal complex is a palladium complex.

The role of the active metal consists in the activation of $CO_2$ and the alkene in order to form a C—C bond between $CO_2$ and the alkene. It is assumed that a metallalactone is formed within the catalytic cycle from the alkene, carbon dioxide and the transition metal complex. The expression "metallalactone" denotes, according to the exchange nomenclature ("a" nomenclature), a lactone (γ-lactone) in which a carbon atom has been exchanged for a metal atom. The expression "metallalactone" should be interpreted broadly and may comprise compounds with structures similar to the Hoberg complex, or related compounds of oligomeric or polymeric structure. The expression shall comprise isolable compounds and (unstable) intermediates.

The metallalactone can be illustrated by the following general formula

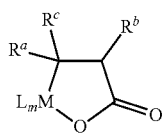

in which
M is the transition metal,
L is a ligand,
m is 1 or 2, and
$R^a$, $R^b$ and $R^c$ are each independently hydrogen, $C_{1-12}$-alkyl, $C_{2-12}$-alkenyl, or $R^a$ and $R^b$ together with the carbon atoms to which they are bonded are a saturated or mono- or diethylenically unsaturated, 5- to 8-membered carbocycle.

It is assumed that the alkoxide deprotonates the metallalactone at the α-carbon atom.

Preferably, the transition metal complex comprises a ligand that coordinates to the transition metal via at least one ligand atom selected from P, N, O, and C. The ligand preferably comprises at least one phosphorus atom which coordinates to the transition metal. The ligand may be monodentate or polydentate, for example bidentate. In general, two monodentate ligands or one bidentate ligand coordinate to the transition metal.

The polydentate, e.g. bidentate, ligand may coordinate to the transition metal to form a four-, five-, six-, seven-, or eight-membered ring, i.e. the transition metal, the atoms which coordinate to the transition metal, and the atoms of the shortest chain which connects the atoms coordinating to the transition metal, together form a four-, five-, six-, seven-, or eight-membered ring. Ligands that coordinate to the transition metal, e.g., nickel or palladium, to form a five-, six-, or seven-membered ring are preferred.

Alternatively, the atoms which coordinate to the transition metal may be directly bound to carbon atoms of two cyclopentadienyl ligands bound to a second metal, e.g., iron.

At least one residue is preferably bound via a secondary or tertiary carbon atom to a transition metal coordinating phosphorus atom. More particularly, at least two residues are preferably bound to the phosphorus atom via a secondary or tertiary carbon atom. Preferred residues bound to the phosphorus atom via a secondary or tertiary carbon atom are adamantyl, tert-butyl, sec-butyl, isopropyl, cyclohexyl, and cyclopentyl.

The ligand is preferably a bidentate P,X ligand in which X is selected from the group consisting of P, N, O, and carbene, in particular a bidentate P,P ligand. The P and X atoms are, for example, separated by a bivalent linker that comprises 2 to 4 bridging atoms. The linker is preferably linked to the P atom by a single bond and linked to the X atom by a single bond and comprises 2 to 4 bridging atoms linked by single bonds.

The bidentate P,X ligand, in particular the bidentate P,P ligand, may be structurally constrained or unconstrained. It is preferably structurally unconstrained.

In the structurally constrained bidentate P,X ligand, in particular in the bidentate P,P ligand, the bridging atoms may be part of at least one cyclic substructure, in particular of at least one 5- to 7-membered cyclic substructure. In preferred bidentate P,P ligands, wherein the bridging atoms are part of at least one 5- to 7-membered cyclic substructure, each bridging atom directly linked to a P atom, together with the P atom to which it is linked, is part of a 5- to 7-membered cyclic substructure; or two neighboring bridging atoms are part of a 5- to 7-membered cyclic substructure.

Preferred structurally constrained bidentate P,P ligands are ligands of formula (IIa)

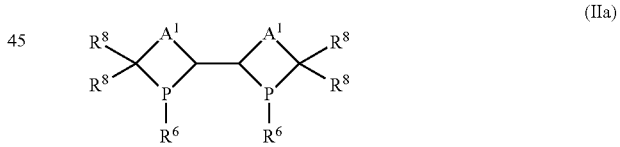

(IIa)

wherein
$R^6$ is independently selected from $CHR^7_2$, $CR^7_3$, $C_3$-$C_{10}$-cycloalkyl, and optionally alkylated aryl having 6 to 18 carbon atoms,
$R^7$ is independently selected from $C_1$-$C_4$-alkyl, preferably linear $C_1$-$C_4$-alkyl,
$A^1$ together with the carbon atoms to which it is bound and the interjacent phosphorous atom forms a 5- to 7-membered cyclic substructure, and
$R^8$ is independently selected from hydrogen, $C_1$-$C_{12}$-alkyl, $C_3$-$C_{12}$-cycloalkyl, $C_3$-$C_{12}$-heterocycloalkyl, $C_6$-$C_{14}$-aryl, $C_6$-$C_{14}$-heteroaryl, $C_1$-$C_{12}$-alkoxy, $C_3$-$C_{12}$-cycloalkoxy, $C_3$-$C_{12}$-heterocycloalkoxy, $C_6$-$C_{14}$-aryloxy, and $C_6$-$C_{14}$-heteroaryloxy.

$A^1$ is preferably selected from —$(CR^8_2)_j$— and —$(CR^9=CR^9)_k$— with both $R^9$ being on the same side of the double bond, wherein $R^8$ is independently selected from H, $C_1$-$C_3$-alkyl, and —O—$C_1$-$C_3$-alkyl, $R^9$ is selected from H and $C_1$-$C_3$-alkyl, or at least two $R^9$ constitute a bridge of one of the formulae:

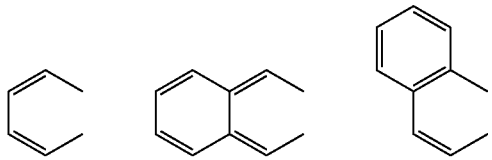

j is 2 or 3, and k is 1 or 2.

$R^6$ is preferably independently selected from $CHR^7_2$, $CR^7_3$, and $C_3$-$C_8$-cycloalkyl, most preferably $CR^7_3$.

$R^7$ is preferably methyl.

$R^8$ is preferably H.

$A^1$ is preferably selected from ethylene, ethenylene, 1,2-phenylene, 1,2-naphthylene, 2,3-naphthylene, and the following formulae:

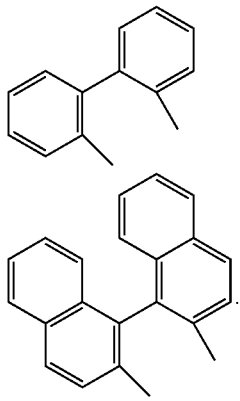

Preferred structurally constrained bidentate P,P ligands are ligands of formula (IIb)

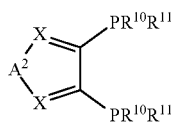

wherein $R^{10}$ is independently selected from linear $C_1$-$C_4$-alkyl, $R^{11}$ is independently selected from $CHR^{10}_2$, $CR^{10}_3$, $C_3$-$C_{10}$-cycloalkyl, and optionally alkylated aryl having 6 to 18 carbon atoms, X is independently selected from C—H, C—$CH_3$, and N, and $A^2$ together with the moieties X to which it is bound and the interjacent carbon atoms forms a 5- to 7-membered cyclic substructure.

$R^{10}$ is preferably independently selected from $C_1$-$C_6$-alkyl and $C_3$-$C_7$-cycloalkyl and $R^{11}$ is $CR^{10}_3$.

$R^{10}$ may, for example, be independently selected from linear $C_1$-$C_4$-alkyl, in particular from linear $C_1$-$C_2$-alkyl.

$R^{11}$ is preferably independently selected from $CHR^{10}_2$, $CR^{10}_3$, and $C_3$-$C_8$-cycloalkyl.

$A^2$ is preferably a —CH=CH— bridge.

X is preferably CH.

Preferred structurally constrained bidentate P,P ligands are ligands of formula (IIc)

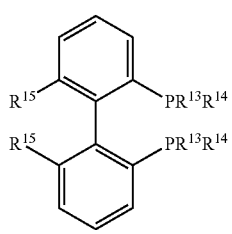

wherein $R^{13}$ and $R^{14}$ are independently selected from $C_3$-$C_{10}$-cycloalkyl, e.g, $C_5$-$C_7$-cycloalkyl, and $R^{15}$ is H, O—$C_1$-$C_6$-alkyl, or both $R_{15}$ together constitute a —CH=CH— bridge.

$R^{15}$ is preferably H or $OCH_3$ and most preferably H.

In the preferred structurally unconstrained bidentate P,X ligand, e.g., bidentate P,P ligand, each of the bridging atoms is unbranched and none of the bridging atoms is part of any cyclic substructure apart from the ring including the transition metal.

In a particularly preferred bidentate P,P ligand, each of the bridging atoms is unbranched and none of the bridging atoms is part of any cyclic substructure apart from the ring including the transition metal. In a particularly preferred bidentate P,P ligand, the P atoms are separated by a linker that comprises 2 bridging carbon atoms, each P atom being linked to the linker and to two secondary carbon bound residues by single bonds, and the bridging carbon atoms being linked by a single bond. The expression "secondary carbon bound residue" refers to a residue that is bound to the P atom via a secondary carbon atom that is comprised by the residue. Each of the four secondary carbon bound residues may be the same or different and preferably selected from secondary $C_3$-$C_{20}$-hydrocarbyl residues wherein any hydrogen atom comprised by the secondary $C_3$-$C_{20}$-hydrocarbyl residues may be substituted by one or multiple non-interfering substituents. A non-interfering substituent is a substituent that is inert under the conditions of the processes according to the invention, i.e. a substituent that does not react with any compound or intermediate being in contact with the ligand in the processes according to the invention. Suitable non-interfereing substituents include, for example, O—$C_1$-$C_6$-alkyl. The secondary $C_3$-$C_{20}$-hydrocarbyl residues are preferably unsubstituted which means that they consist of hydrogen and carbon atoms. Preferred unsubstituted secondary $C_3$-$C_{20}$-hydrocarbyl residues are 2-propyl, 2-butyl, 2-pentyl, 3-pentyl, cyclopentyl, cyclohexyl, and cycloheptyl. The preferred linker is —$CH_2$—$CH_2$—.

Preferred structurally unconstrained bidentate P,P ligands are ligands of formula (IId)

wherein $R^{16}$ and $R^{17}$ are independently an unbranched or branched, acyclic or cyclic, aliphatic residue having 1 to 20 carbon atoms, where individual carbon atoms may independently be replaced by a hetero group selected from the group of —O— and >N—, individual hydrogen atoms may independently be replaced by Cl, or F, and any two residues bound to the same phosphorous atom may be covalently bound to one another, e is 1, 2, 3, 4, or 5, preferably 2, 3, or 4, $R^{18}$ is independently selected from H, $C_1$-$C_8$-alkyl, $C_1$-$C_8$-alkoxy, $C_3$-$C_{10}$-cycloalkyl, $C_3$-$C_{10}$-cycloalkoxy, $C_6$-$C_{10}$-aryl, and $C_6$-$C_{10}$-aryloxy, and $R^{19}$ is independently selected from H, $C_1$-$C_8$-alkyl, $C_3$-$C_{10}$-cycloalkyl, and $C_6$-$C_{10}$-aryl.

Preferably, $(CR^{18}R^{19})_e$ is —CH$_2$—CH$_2$—, —CH$_2$—CH$_2$—CH$_2$—, or —CH$_2$—CH$_2$—CH$_2$—CH$_2$—.

$R^{16}$ and $R^{17}$ are preferably independently $C_1$-$C_{20}$-alkyl, or $C_3$-$C_{20}$-cycloalkyl, wherein $C_1$-$C_{20}$-alkyl is unsubstituted or substituted with 1, 2, 3, or 4 substituents independently selected from Cl, F, and $C_1$-$C_4$-alkoxy and wherein $C_3$-$C_{20}$-cycloalkyl is unsubstituted or substituted with 1, 2, 3, or 4 substituents independently selected from Cl, F, $C_1$-$C_8$-alkyl and $C_1$-$C_4$-alkoxy.

$R^{16}$ and $R^{17}$ are most preferably independently methyl, ethyl, 1-propyl, 2-propyl, 1-butyl, 2-butyl, tert-butyl, 1-(2-methyl)propyl, 1-pentyl, 1-(2-methyl)pentyl, 1-hexyl, 1-(2-ethyl)hexyl, 1-heptyl, 1-(2-propyl)heptyl, 1-octyl, 1-nonyl, 1-decyl, 1-undecyl, 1-dodecyl, adamantyl, cyclopentyl, methylcyclopentyl, cyclohexyl, methylcyclohexyl, cycloheptyl, cyclooctyl, or norbornyl, in particular independently 2-propyl, 2-butyl, tert-butyl, adamantyl, cyclopentyl, methylcyclopentyl, cyclohexyl, methylcyclohexyl, cycloheptyl, cyclooctyl, or norbornyl.

Particularly preferred bidentate P, P ligands are ligands of formula (IId-1)

$$R^{16}R^{17}P—(CR^{18}H)_e—PR^{16}R^{17} \quad \text{(IId-1)}$$

wherein $R^{16}$ and $R^{17}$ are each independently an unbranched or branched, acyclic or cyclic aliphatic residue having 1 to 20 carbon atoms, e is 2, 3, or 4, and $R^{18}$ is independently selected from H, $C_1$-$C_8$-alkyl, $C_1$-$C_8$-alkoxy, $C_3$-$C_{10}$-cycloalkyl, $C_3$-$C_{10}$-cycloalkoxy, $C_6$-$C_{10}$-aryl, and $C_6$-$C_{10}$-aryloxy, and preferably H.

In a particularly preferred process according to the invention, the ligand is selected from 1,2-bis(dicyclohexylphosphino)ethane, 1,3-bis(dicyclohexylphosphino)propane, 1,4-bis(dicyclohexylphosphino)butane, 1,2-bis(dicyclopentylphosphino)ethane, 1,3-bis(dicyclopentylphosphino)propane, 1,4-bis(dicyclopentylphosphino)butane, 1,2-bis(dicycloheptylphosphino)ethane, 1,3-bis(dicycloheptylphosphino)propane, 1,4-bis(dicycloheptylphosphino)butane, 1,2-bis(diisopropylphosphino)ethane, 1,3-bis(diisopropylphosphino)propane, 1,4-bis(diisopropylphosphino)butane, 1,2-bis(di-sec-butylphosphino)ethane, 1,3-bis(di-sec-butylphosphino)propane, 1,4-bis(di-sec-butyl phosphino)butane, 1,2-bis(dodecylphosphino)ethane, 1,3-bis(dodecylphosphino)propane, 1,4-bis(dodecylphosphino)butane, 1,2-bis(decylphosphino)ethane, 1,3-bis(decylphosphino)propane, 1,4-bis(decylphosphino)butane, 1,2-bis(tetradecylphosphino)ethane, 1,3-bis(tetradecylphosphino)propane, 1,4-bis(tetradecylphosphino)butane, 1,2-bis(hexadecylphosphino)ethane, 1,3-bis(hexadecylphosphino)propane, 1,4-bis(hexadecylphosphino)butane, 1,2-bis(di-tert-butylphosphino)ethane, 1,3-bis(di-tert-butylphosphino)propane, 1,4-bis(di-tert-butylphosphino)butane, and

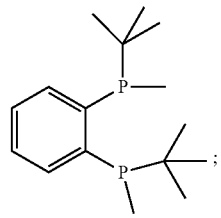 [SMILES: CP(c1ccccc1P(C)C(C)(C)C)C(C)(C)C]

preferably from 1,2-bis(dicyclohexylphosphino)ethane, 1,2-bis(diisopropylphosphino)ethane, 1,2-bis(dodecylphosphino)ethane, 1,2-bis(di-tert-butylphosphino)ethane, 1,2-bis(dicyclopentylphosphino)ethane, and

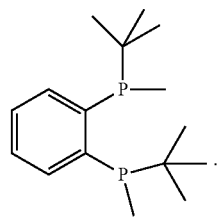 [SMILES: CP(c1ccccc1P(C)C(C)(C)C)C(C)(C)C]

Suitable ligands are, for example, bidentate and multidentate ligands that comprise one or two coordinating phosphorous atoms and an additional carbon atom or hetero atom that is bound to the transition metal. Preferably, a 5-membered ring is formed, when the additional carbon atom or hetero atom binds to the transition metal, as for example with (diphenylphosphino)acetate known from the SHOP-Process or with 2-(dimethylphosphino)-N,N-dimethylethanamine. Specific bidentate ligands are ligands of formula (IIg)

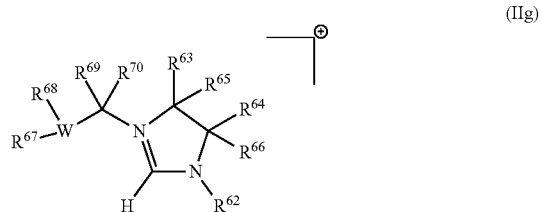

wherein

W is phosphorous (P) or phosphite (P=O), $R^{62}$, is independently an unbranched or branched, acyclic or cyclic, aliphatic, araliphatic or aromatic residue having 1 to 16 carbon atoms, where individual carbon atoms may independently be replaced by a hetero group selected from the group of —O— and >N—, and where individual hydrogen atoms may independently be replaced by Cl or F, $R^{63}$ and $R^{64}$ are independently an unbranched or branched, acyclic or cyclic, aliphatic, araliphatic or aromatic residue having 1 to 16 carbon atoms, where individual carbon atoms may independently be replaced by a hetero group selected from the group of —O— and >N—, individual hydrogen atoms may independently be replaced by Cl, Br, I, or F, and both residues may be covalently bound to one another, $R^{65}$ and $R^{66}$ together are a chemical bond, or as defined for $R^{63}$ and $R^{64}$ $R^{67}$ and $R^{68}$ are as defined for $R^{63}$ and $R^{64}$, and
$R^{69}$ and $R^{70}$ are as defined for $R^{63}$ and $R^{64}$.

Preferably $R^{63}$, $R^{64}$, $R^{65}$ and $R^{66}$ are independently hydrogen, $C_1$-$C_{12}$-alkyl, or $C_1$-$C_{14}$-aryl; or $R^{63}$ and $R^{64}$ are independently hydrogen, $C_1$-$C_{12}$-alkyl, or $C_1$-$C_{14}$-aryl, and $R^{65}$ and $R^{66}$ together are a chemical bond; or $R^{63}$ and $R^{64}$ are independently hydrogen, or methyl, and $R^{65}$ and $R^{66}$ together are a $C_3$-$C_{10}$-alkane-1,3-diyl, $C_3$-$C_{10}$-alkane-1,4-diyl, or $C_3$-$C_{10}$-alkane-1,3-diyl bridge; or $R^{65}$ and $R^{66}$ together are a chemical bond, and $R^{63}$, and $R^{64}$, together with the carbon atoms to which they are bound, are part of a monocyclic or bicyclic aromatic ring system.

$R^{62}$, $R^{67}$ and $R^{68}$ are preferably independently $C_1$-$C_{12}$-alkyl, $C_3$-$C_{12}$-cycloalkyl, or $C_3$-$C_{14}$-aryl, wherein $C_3$-$C_{12}$-cycloalkyl and $C_3$-$C_{14}$-aryl are unsubstituted or substituted with 1, 2, 3, or 4 substituents independently selected from Cl, F, $C_1$-$C_8$-alkyl and $C_1$-$C_4$-alkoxy.

$R^{62}$, $R^{67}$ and $R^{68}$ are most preferably independently methyl, ethyl, 1-propyl, 2-propyl, 1-butyl, 2-butyl, tert-butyl, 1-(2-methyl)propyl, 2-(2-methyl)propyl, 1-pentyl, 1-(2-methyl)pentyl, 1-hexyl, 1-(2-ethyl)hexyl, 1-heptyl, 1-(2-propyl)heptyl, 1-octyl, 1-nonyl, 1-decyl, 1-undecyl, 1-dodecyl, adamantyl, cyclopentyl, methylcyclopentyl, cyclohexyl, methylcyclohexyl, cycloheptyl, cyclooctyl, norbornyl, phenyl, napthyl, tolyl, xylyl, chlorophenyl or anisyl.

The ligand may also be a bidentate or multidentate ligand that comprises one or two coordinating nitrogen atoms and an additional carbon atom that is bound to the transition metal. Preferably, a 5-membered ring is formed, when the additional carbon atom binds to the transition metal, as for example with 2-phenylpyridine or 6-phenyl-2,2'-bipyridine.

Suitable tridentate ligands are, for example, ligands of formula (IIh)

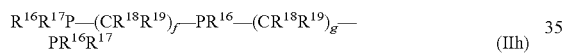

(IIh)

wherein
$R^{16}$, $R^{17}$, $R^{18}$, and $R^{19}$ are each as already defined, and
f and g are independently 1, 2, 3, 4, or 5, preferably 2, 3, or 4.

Exemplary tridentate ligands are ((methylphosphinediyl)bis-(methylene))bis(dimethylphosphine), ((ethylphosphindiyl)bis(methylene))bis(diethyl-phosphine), and ((methylphosphinediyl)bis(methylene))bis(diphenylphosphine).

In addition to the above-described ligands, the transition metal complex may also have at least one further ligand selected from the alkoxide, the alcohol byproduct which is the conjugate acid of the alkoxide, halides, amines, amides, oxides, phosphides, carboxylates, acetylacetonate, aryl- or alkylsulfonates, hydride, CO, olefins, dienes, cycloolefins, nitriles, aromatics and heteroaromatics, ethers, $PF_3$, phospholes, and mono-, di- and polydentate phosphinite, phosphonite, phosphoramidite and phosphite ligands.

Any of these further ligands can be displaced when the alkene and carbon dioxide are reacted.

The transition metal complex, e.g., palladium or nickel complex, may for example be obtained from the ligand and the transition metal, e.g., palladium or nickel, or from the ligand and a transition metal source, e.g., palladium or nickel source, comprising the transition metal, e.g., palladium or nickel, at oxidation state 0. Alternatively, the transition metal complex may for example be obtained by reducing a salt of the transition metal with a reducing agent, e.g., $H_2$, Mg, Na or Zn.

Palladium sources include, for example, $PdL_2$, $PdL_4$, $LPdX_2$, $L_2PdX_2$, $L_2Pd_2X_2$, $L_2Pd_2X_4$, $Pd_3X_6$, $L_3Pd_2$, $L_2Pd_2$, wherein
X is selected from halide, pseudohalide, carboxylate, alkoxide, carbonate, sulfate, nitrate, hydroxide, acetylacetonate, cyclopentadiene, alkyl, and aryl, and L is a neutral ligand selected from phosphine, amine, olefin, carbonyl and nitrile, and the corresponding adducts with solvents such as ethers, DMSO, or water.

The palladium sources and salts are preferably selected from [$Pd_2(Allyl)_2(Cl)_2$], [$Pd_2(Methallyl)_2(Cl)_2$] [$Pd(dba)_2$], [$Pd_2(dba)_3$], $PdCl_2$, $PdBr_2$, $PdI_2$, $Pd(NO_3)_2$, $PdSO_4$ [$Pd(OAc)_2$], [$Pd(PtBu_3)_2$], [$Pd(PCy_3)_2$], [$Pd(PoTolyl_3)_2$], [$Pd(PPh_3)_4$], [$Pd(COD)(Cl)(Me)$], [$Pd(Phen)(OAc)_2$], [$Pd_2(PtBu_3)_2(Br)_2$], [$Pd(C_6H^5CN)_2(Cl)_2$], [$Pd(PCy_3)_2(Cl)_2$], [$Pd(PPh_3)_2(Cl)_2$], [$Pd(norbornadiene)(Cl)_2$], [$Pd(TMEDA)(Cl)_2$], [$Pd(TMEDA)(CH_3)_2$], [$Pd_3(OAc)_6$], [$Pd(CF_3COO)_2$], [$Pd(Acetylactonate)_2$], [$Pd(COD)(Cl)_2$], and [$Pd(Allyl)(Cp)$].

Nickel sources and salts include, for example, $NiL_2$, $NiL_4$, $LNiX_2$, $L_2NiX_2$, $L_2Ni_2X_2$ wherein X and L are as defined above and the corresponding adducts with solvents such as ethers, DMSO, or water.

The nickel sources and salts are preferably selected from [$Ni(COD)_2$], $NiF_2$, $NiCl_2$, $NiBr_2$, $NiI_2$, [$Ni(OAc)_2$], [$Ni(Acetylactonate)_2$], [$Ni(Ph_3P)_2(Cl)_2$], [$Ni((PPh_2)_2Fc)(Cl)_2$], [$Ni_2(Methallyl)_2(Cl)_2$], [$Ni_2(allyl)_2(Cl)_2$], [$Ni(CO)_4$], [$Ni(PPh_3)_2(CO)_2$], [$Ni(NO_3)_2$], [$Ni(OH)_2$], [$Ni(PPh_3)_4$], [$Ni(CF_3COO)_2$], [$Ni(SO_4)$], [$Ni(2-ethylhexanoate)_2$], [$Ni(P(OPh)_3)_4$], [$Ni(C_7H_{15}COO)_2$], [$Ni(Cp)_2$], [$Ni(PCy_3)_2(Cl)_2$], [$Ni(PMe_3)_2(Cl)_2$], [$Ni(PBu_3)_2(Br)_2$], and [$Ni(dppe)(Cl)_2$].

Abbreviations used in the above palladium and nickel sources and salts:
dba is dibenzylideneacetone
Cy is Cyclohexyl
COD is 1,5-Cyclooctadiene
Phen is Phenanthroline
TMEDA is N,N,N',N'-tetramethylethylenediamine
Fc is Ferrocenyl
Cp is Cyclopentadienyl Many of the above palladium and nickel sources and salts are commercially available.

Suitable alkenes are those of the following general formula

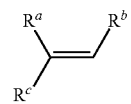

wherein
$R^a$, $R^b$ and $R^c$ are each independently hydrogen, $C_{1-12}$-alkyl, $C_{2-12}$-alkenyl, or $R^a$ and $R^b$ together with the carbon atoms to which they are bonded are a monoethylenically or diethylenically unsaturated, 5- to 8-membered carbocycle.

Suitable alkenes are, for example, ethene, propene, isobutene, butadiene, piperylene, 1-butene, 1-pentene, 1-hexene, 1-heptene, 1-octene, 1-nonene, 1-decene, 2-butene, cyclopentene, cyclohexene, cycloheptene, cyclooctene, cyclooctadiene, or styrene. The alkene to be used in the process according to the invention is generally gaseous or liquid under the reaction conditions.

In a preferred embodiment, the alkene is ethene. The process according to the invention makes it possible to obtain an acrylate.

In another embodiment, the alkene is piperylene and a sorbate is obtained.

In step a) the alkene partial pressure is, for example, in the range from 0.5 bar to 200 bar, preferably from 1 bar to 100 bar, in particular from 2 bar to 80 bar, further preferred from 3 bar to 60 bar, most preferably from 5 to 50 bar.

All pressures indicated herein are absolute pressures.

The $CO_2$ for use in step a) of the process according to the invention can be used in gaseous, liquid or supercritical form. It is also possible to use carbon dioxide-comprising gas mixtures available on the industrial scale, provided that they are substantially free of carbon monoxide.

$CO_2$ and alkene may also comprise inert gases such as nitrogen or noble gases. Advantageously, however, the content thereof is below 10 mol %, based on the total amount of carbon dioxide and alkene in the reactor.

The molar ratio of carbon dioxide to alkene in step a) is generally in the range from 0.1 to 10 and preferably in the range from 0.5 to 5. The carbon dioxide and the alkene are generally fed into step a) in a molar ratio in the range from 0.1 to 10 and preferably in the range from 0.5 to 5 moles of carbon dioxide per mole of alkene.

The specific structure of the alkoxide determines the solubility of the alkoxide and of the alcohol byproduct which is the conjugate acid of the alkoxide in polar and nonpolar phases. The solubility of the alkoxide in polar and nonpolar phases may be controlled by the length, size and number of alkyl and cycloalkyl moieties comprised by the alkoxide.

Step a) of the process of the invention is preferably carried out in the presence of alkali metal or alkaline earth metal cations. Preferred alkali metal cations are $Na^+$, $Li^+$, and $K^+$. Preferred alkaline earth metal cations are $Mg^{2+}$ and $Ca^{2+}$. The cations are not necessarily fully dissolved in the reaction medium. The alkali metal or alkaline earth metal cations may, for example, be added together with the alkoxide in the form of an alkali metal or alkaline earth metal salt of the alkoxide.

It may happen that part of the carboxylation catalyst is deactivated by oxidation of the active metal, e.g., nickel. The deactivation reduces the overall efficiency of the process. In this case, a reducing agent can be added. Apparently, the reducing agent reactivates the deactivated carboxylation catalyst by reduction of the oxidized active metal. Any reducing agent which is capable of reducing the deactivated carboxylation catalyst is suitable as the reducing agent. Preferable reducing agents are $H_2$, Mg, Na and Zn, or Phosphines.

In preferred embodiments, the transition metal complex is present in homogeneous solution in the reaction medium in the form of complex-type compounds.

The reaction medium wherein the alkene and carbon dioxide are reacted in step a) preferably comprises 0.1 to 20000 ppm by weight, preferably 1 to 1000 ppm by weight, in particular 5 to 500 ppm by weight of the transition metal, based on the total weight of the reaction medium.

Preferably, step a) is carried out in an aprotic organic solvent. Suitable aprotic organic solvents are in principle those which (i) are chemically inert with regard to the carboxylation of the alkene, (ii) in which the alkoxide and the carboxylation catalyst have good solubility, and (iii) which are immiscible or only have limited miscibility with the polar solvent as specified below. The aprotic organic solvent is preferably an aliphatic, aromatic or araliphatic hydrocarbon or an ether, for example octane, nonane, decane, undecane, dodecane, tridecane, tetradecane, pentadecane, hexadecane, heptadecane, octadecane, benzene, toluene, xylene, chlorobenzene, anisole, butyl-phenyl-ether, diphenylether, dibutylether, ethylenglcyoledibutlyether, diethylether, tetrahydrofuran, 2-methyl-tetrahydrofuran or mixtures thereof.

Step a) is preferably carried out in a reactor which is suitable for gas/liquid reactions or liquid/liquid reactions at the given temperature and the given pressure. Suitable standard reactors for gas-liquid reaction systems are specified, for example, in K. D. Henkel, "Reactor Types and Their Industrial Application", in Ullmann's Encyclopedia of Industrial Chemistry 2005, Wiley VCH Verlag GmbH & Co KGaA, DOI: 10.1002114356007.b04_087, chapter 3.3 "Reactors for gas-liquid reactions". Examples include stirred tank reactors, tubular reactors or bubble columns.

Step a) of the process according to the invention may be performed continuously or discontinuously. Step a) is preferably performed continuously.

In a discontinuous step a), the ligand, the transition metal which may for example be in the form of the transition metal source, the alkoxide, carbon dioxide and the alkene are given into the reactor. Preferably, gaseous carbon dioxide and gaseous alkene are passed into the reactor at the desired pressure. After the reaction has slowed down, the pressure may be reduced.

Step a) may, for example, be performed at a total pressure in the range from 1 to 300 bar, preferably from 3 to 200 bar, in particular from 5 to 150 bar. Step a) may, for example, be performed at temperatures in the range from 20 to 250° C., in particular from 40 to 200° C., preferably from 50 to 190° C., further preferably from 60 to 180° C., most preferably from 70 to 180° C.

In order to achieve good mixing of the alkene, carbon dioxide, the carboxylation catalyst, and the alkoxide, suitable apparatuses can be used in step a). Such apparatuses may be mechanical stirrer apparatuses with one or more stirrers, with or without baffles, packed or nonpacked bubble columns, packed or nonpacked flow tubes with or without static mixers, or other useful apparatuses known to those skilled in the art for such a process step. The optional use of baffles and delay structures is explicitly included in the process according to the invention.

$CO_2$, alkene and the alkoxide can be fed into step a) either together or spatially separately. Such a spatial separation can be accomplished, for example in a stirred tank, in a simple manner by means of two or more separate inlets. When more than one tank is used, for example, there may be different media charges in different tanks. Separation of the addition of the $CO_2$ and alkene reactants in terms of time is also possible in step a) of the process according to the invention. Such a time separation can be accomplished, for example, in a stirred tank by staggering the charging with the reactants. In the case of use of flow tubes or apparatus of a similar kind, such charging can be effected, for example, at different sites in the flow tube; such a variation of the addition sites is an elegant way of adding the reactants as a function of residence time.

In step a) of the process according to the invention, there is no need of separately feeding the $CO_2$, the alkene and the alkoxide to the reaction.

One or more immiscible or only partly miscible liquid phases can be used. The optional use of supercritical media and ionic liquids and the establishment of conditions which promote formation of such states are explicitly incorporated into step a) of the process.

The optional application of phase transfer catalysis and/or the use of surfactants can be incorporated into step a) of the process according to the invention.

The alkoxide is consumed stoichiometrically when the alkene and carbon dioxide are reacted in step a) of the process according to the invention. The alkoxide is protonated such that an alcohol byproduct which is the conjugate acid of the alkoxide is obtained.

The amount of alkoxide used in the process according to the invention is generally 5 to 95% by weight, preferably 20 to 60% by weight, and most preferably 5 to 25% by weight, based on the overall reaction medium in the reactor.

It is possible to use the alkoxide in substoichiometric amounts based on the carboxylation catalyst in step a). Even when substoichiometric amounts of the alkoxide are used, it is possible to obtain excess α,β-ethylenically unsaturated carboxylic acid salt as based on the catalyst concentration, if the alkoxide is regenerated and recycled into step a) as described below.

In step b) of the process according to the invention, at least part of the crude reaction product obtained in step a) is contacted with a polar solvent such that a first liquid phase in which the α,β-ethylenically unsaturated carboxylic acid salt is enriched, and a second liquid phase in which the carboxylation catalyst is enriched, are obtained.

"Enriched" is understood to mean a partition coefficient P of each of the carboxylation catalyst, and the α,β-ethylenically unsaturated carboxylic acid salt of >1.

$$P_1 = \frac{\left[\begin{array}{l}\text{Concentration of the carboxylation}\\ \text{catalyst in the second liquid phase}\end{array}\right]}{\left[\begin{array}{l}\text{Concentration of the carboxylation}\\ \text{catalyst in the first liquid phase}\end{array}\right]}$$

$$P_2 = \frac{\left[\begin{array}{l}\text{Concentration of the } \alpha, \beta\text{-ethylenically unsaturated}\\ \text{carboxylic acid salt in the first liquid phase}\end{array}\right]}{\left[\begin{array}{l}\text{Concentration of the } \alpha, \beta\text{-ethylenically unsaturated}\\ \text{carboxylic acid salt in the second liquid phase}\end{array}\right]}$$

The partition coefficient $P_1$ is preferably ≥10 and more preferably ≥20, further preferably ≥100, most preferably ≥1000, for example ≥10000.

The partition coefficient $P_2$ is preferably ≥10 and more preferably ≥20, further preferably ≥100, most preferably ≥1000, for example ≥10000.

The alcohol byproduct can be enriched either in the first or second liquid phase obtained in step b).

Only the alcohol byproduct comprised by the first liquid phase is distilled off in step c) and then in optional step d) contacted with an alkaline material in order to regenerate the alkoxide which can then be recycled to step a).

As described in further detail below, the second liquid phase can be recycled to step a) with or without regenerating the alkoxide from the alcohol byproduct comprised by the second liquid phase. The second liquid phase is, for example, recycled to step a) without alkoxide regeneration if only a low proportion of the alcohol byproduct is comprised by the second liquid phase. It may be sufficient to recycle to step a) (via steps c) and d)) only the alcohol byproduct comprised by the first liquid phase in the form of regenerated alkoxide, in particular, if only a low proportion of the alcohol byproduct is comprised by the second liquid phase.

It is thus preferable if a significant proportion of the alcohol byproduct is comprised by the first liquid phase obtained in step b). According to the invention, at least 5% by weight of the alcohol byproduct, preferably at least 10% by weight of the alcohol byproduct, in particular at least 15% by weight of the alcohol byproduct, most preferably at least 20% by weight of the alcohol byproduct is comprised by the first liquid phase.

Owing to the rapid separation of the α,β-ethylenically unsaturated carboxylic acid salt from the catalyst in step b), a reverse reaction with decomposition to carbon dioxide and alkene is suppressed. In addition, losses of active metal are low as the catalyst is retained in the second liquid phase.

Preferably, the main constituent of the second liquid phase is the aprotic organic solvent as specified above.

The carboxylation catalyst is generally selected by a simple experiment in which the partition coefficient of the desired catalyst is determined experimentally under the planned process conditions.

Any polar solvent in which the α,β-ethylenically unsaturated carboxylic acid salt has good solubility and which has zero or only limited miscibility with the second liquid phase, e.g., with the aprotic organic solvent as specified above, in which the carboxylation catalyst is enriched, is suitable. The polar solvent should be selected such that the polar solvent is present in enriched form in the first liquid phase. "Enriched" is understood to mean a proportion by weight of >50% of the polar solvent in the first liquid phase based on the total amount of polar solvent in both liquid phases. The proportion by weight is preferably >90%, more preferably >95% and most preferably >97%. The polar solvent is generally selected by simple tests in which the partition of the polar solvent in the two liquid phases is determined experimentally under the process conditions.

Substance classes which are suitable as polar solvents are water, alcohols, diols and the carboxylic esters thereof, polyols and the carboxylic esters thereof, sulfones, sulfoxides, open-chain or cyclic amides, and mixtures of the substance classes mentioned.

Examples of suitable alcohols are methanol, ethanol, 1-propanol, isopropanol, tert-butanol and butanol. Examples of suitable diols and polyols are ethylene glycol, diethylene glycol, triethylene glycol, polyethylene glycol, 1,3-propanediol, 2-methyl-1,3-propanediol, 1,4-butanediol, dipropylene glycol, 1,5-pentanediol, 1,6-hexanediol and glycerol.

Examples of suitable sulfoxides are dialkyl sulfoxides, preferably $C_1$- to $C_6$-dialkylsulfoxides, especially dimethyl sulfoxide.

Examples of suitable open-chain or cyclic amides are formamide, N-methylformamide, N,N-dimethylformamide, N-methylpyrrolidone, acetamide and N-methylcaprolactam.

The polar solvent is preferably selected from polar solvents that have a boiling temperature of less than 150° C. at a pressure of 1 bar.

In a preferred embodiment, the polar solvent is an aqueous phase or an alcohol. In a particularly preferred embodiment, the polar solvent comprises at least 90% by weight of water, for example, at least 95% by weight of water.

In order to remove the first liquid phase, one may, for example, conduct only the first liquid phase out of the carboxylation reactor and leave the second liquid phase within the carboxylation reactor.

Alternatively, one may conduct a liquid-liquid mixed-phase stream out of the carboxylation reactor. Preferably, crude reaction product is conducted out of the carboxylation reactor and this crude reaction product is then brought into contact with the polar solvent. The liquid-liquid phase separation can then be performed in a suitable apparatus outside the carboxylation reactor.

The two liquid phases are generally separated by gravimetric phase separation in step b). Suitable examples for this purpose are standard apparatus and standard methods which can be found, for example, in E. Müller et al., "Liquid-Liquid Extraction", in Ullmann's Encyclopedia of Industrial Chemistry, 2005, Wiley-VCH Verlag GmbH & Co. KGaA, DOI:10.1002/14356007.b03_06, chapter 3 "Apparatus". In general, the first liquid phase enriched with the α,β-ethylenically unsaturated carboxylic acid salt is heavier and forms the lower phase.

Supercritical media and ionic liquids, and the establishment of conditions which promote the formation of such states, may be applied for phase separation. Preferably, the phase separation of the first and the second liquid phase is facilitated by changing temperature and/or pressure.

Liquid-liquid extraction can be effected in all apparatus suitable for this purpose, such as stirred vessels, extractors or percolators.

Step b) may be performed continuously or discontinuously. It is preferably performed continuously.

Step b) may, for example, be performed at the same or lower total pressure than step a). Step b) is preferably performed at lower total pressure than step a). The crude reaction product obtained from step a) may, for example, be decompressed into a decompression vessel before it is directed into step b). Any gas released from the crude reaction product during decompression, i.e. $CO_2$ and optionally alkene, is preferably recycled into the process, in particular into step a). Step b) is preferably performed at a total pressure in the range from 0.01 to 20 bar, for example in the range from 0.1 to 10 bar.

In step c) of the process according to the invention, the alcohol byproduct is distilled off from the first liquid. This provides a first distillation fraction comprising most of the alcohol byproduct, preferably at least 90%, more preferably at least 95%, in particular at least 97%, most preferably at least 99% of the alcohol byproduct comprised by the first liquid phase being fed into step c).

It is preferable to distill off both, the alcohol byproduct, and the polar solvent from the first liquid phase being fed into step c) such that the α,β-ethylenically unsaturated carboxylic acid salt is obtained as a distillation residue. Accordingly, in step c) at least a part of the polar solvent is distilled off from the first liquid phase. This yields a second distillation fraction comprising most of the polar solvent, preferably at least 90%, more preferably at least 95%, in particular at least 97%, most preferably at least 99% of the polar solvent comprised by the first liquid phase being fed into step c).

Step c) may, for example, be carried out in a distillation unit comprising a distillation column which may comprise trays or packing material. The first liquid phase is fed into the distillation unit, where it is heated and/or exposed to reduced pressure. The first and the second distillation fraction have different boiling temperatures and are released from the distillation column at different levels.

The pressure in step c) is, for example, in the range from 0.0001 to 10 bar, preferably in the range from 0.001 to 5 bar, most preferably in the range from 0.01 to 2 bar. The temperature in the bottom of the distillation column is preferably kept well above the boiling temperature of the alcohol byproduct at the distillation pressure, and, if the polar solvent is also distilled of, also well above the boiling temperature of the polar solvent at the distillation pressure. The temperature in the bottom of the distillation column is, for example, in the range from 60 to 200° C., preferably in the range from 80 to 180° C.

Step c) may be performed continuously or discontinuously. It is preferably performed continuously.

The polar solvent recovered in step c) is preferably used as the polar solvent in step b). The second distillation fraction, i.e. the distillation fraction comprising most of the polar solvent, may, for example be used as the polar solvent in step b) without further workup of the second distillation fraction.

A preferred process according to the invention comprises step d) wherein at least part of the alcohol byproduct recovered in step c) is contacted with an alkaline material in order to regenerate the alkoxide. In step d), the alkoxide is regenerated by reacting the alcohol byproduct with an alkaline material which is capable of deprotonating the alcohol byproduct such that the alkoxide is regenerated.

The alcohol byproduct is comprised by a distillation fraction that is obtained outside of the carboxylation reactor. It can therefore be contacted with the alkaline material outside of the carboxylation reactor, i.e. at low carbon dioxide partial pressure. Nucleophilic alkaline materials that are inactivated at the conditions of the reaction between alkene and carbon dioxide, i.e. at high carbon dioxide partial pressure, may thus be used for regenerating the alkoxide. This is advantageous as some of these alkaline materials, for example, sodium hydroxide, are less costly than other less nucleophilic alkaline materials.

The alkaline material used in step d) is preferably selected from alkali metals or alkaline earth metals, alkali metal and alkaline earth metal oxides and alkali metal and alkaline earth metal hydroxides and their mixtures, in particular from Li, Na, K, Ca, $Li_2O$, $Na_2O$, $K_2O$, CaO, LiOH, NaOH, KOH, $Ca(OH)_2$, and their mixtures. Sodium hydroxide is the most preferred alkaline material used in step d).

Alternative alkaline materials that can be used in step d) are, for example, selected from alkali metal or alkaline earth metal hydrides, amides, phosphides, silanolates, alkyls, and aryls. These are similarly or even more reactive towards the alcohol byproduct but more difficult to handle and/or more costly than the aforementioned preferred alkaline materials.

Suitable alkali metal or alkaline earth metal hydrides are, for example, lithium hydride, sodium hydride, potassium hydride, magnesium hydride, and calcium hydride.

Suitable alkali metal or alkaline earth metal amides are, for example, $LiNH_2$, $NaNH_2$, $KNH_2$, $LiNMe_2$, $LiNEt_2$, $LiN(iPr)_2$, $NaNMe_2$, $NaNEt_2$, $NaN(iPr)_2$, $KNMe_2$, $KNEt_2$, $KN(iPr)_2$, (Me=Methyl; Et=Ethyl; iPr=Isopropyl). The suitable amides also include silicon-containing amides such as sodium hexamethyldisilazide (NaHMDS), potassium hexamethyldisilazide (KHMDS) or lithium hexamethyldisilazide (LiHMDS).

Suitable alkali metal or alkaline earth metal phosphides are, for example, those of the formula $M^2PR^{101}_2$ in which $M^2$ is an alkali metal or an equivalent of an alkaline earth metal, and $R^{101}$ is $C_{1-12}$-alkyl or $C_6$-$C_{10}$-aryl, for example $KPPh_2$ or $NaPPh_2$ (Ph=Phenyl).

Suitable alkali metal or alkaline earth metal silanolates are, for example, those of the formula $M^2OSi(C_{1-4}$-Alkyl$)_3$ in which $M^2$ is an alkali metal or an equivalent of an alkaline earth metal, for example $NaOSiMe_3$.

Suitable alkali metal or alkaline earth metal alkyls or aryls are, for example, lithium alkyl and lithium aryl compounds, such as methyllithium, n-butyllithium, sec-butyllithium, tert-butyllithium, phenyllithium, where the benzene ring may bear substituents at any position (e.g. $OCH_3$, $CH_2NMe_2$, $CONR_2$), cyclohexyllithium, where the cyclohexyl ring may comprise heteroatoms (e.g. O, N, S), ethyllithium, lithium pentadienyl, lithium 2-furanyl, lithium 2-thiophenyl, lithium ethynyl. Also suitable are sodium alkyl and sodium aryl compounds, such as sodium cyclopentadienyl.

The suitable alkaline earth metal alkyls and aryls include magnesium alkyl and magnesium aryl compounds (Grignard reagents) of the general formula $R^{102}MgX$, where $R^{102}$ may be one of the alkyl and aryl residues listed above for the lithium alkyl and lithium aryl compounds and X may be F, Cl, Br, I.

When the alkaline material is selected from alkali or alkaline earth metals, such as sodium, lithium, or potassium, in particular sodium, the deprotonation of the alcohol byproduct is coupled with a redox reaction. The alkali or alkaline earth metal is oxidized to the alkali metal or alkaline earth metal cation and the oxygen-bound proton of the alcohol byproduct is reduced to hydrogen.

The regeneration of the alkoxide is preferably performed in the liquid or supercritical phase at pressures in the range from 0.0001 to 150 bar, preferably from 0.001 to 100 bar, more preferably from 0.001 to 60 bar. The temperature may, for example, be in the range from −20 and 300° C., preferably from 20 to 250° C., more preferably from 40 to 200° C.

In a preferred embodiment, water is removed in step d), in particular when the alkaline material is selected from alkali or alkaline earth metal oxides and hydroxides. The removal of water is, for example, achieved by evaporating the water, e.g., by distillation. Step d) is then preferably carried out in a second distillation unit. When an alkali metal or alkaline earth metal hydroxide is used as alkaline material, the regeneration of the alkoxide requires a continuous removal of the water that is formed as a byproduct. The continuous removal of the water being formed as a byproduct is achieved, e.g., by evaporating or distilling off water, for example, by azeotropic distillation of the water, e.g., with benzene, toluene, or the alcohol byproduct itself, as described, for example, in chapter 4.2 of Falbe, J., Bahrmann, H., Lipps, W., Mayer, D. and Frey, G. D. 2013, Ullmann's Encyclopedia of Industrial Chemistry, DOI: 10.1002/14356007.a01_279, or in DE 968 903.

Step d) may be performed continuously or discontinuously. It is preferably performed continuously.

In a preferred process according to the invention, at least part of the regenerated alkoxide obtained in step d) is recycled to step a). The regenerated alkoxide obtained in step d) may, for example, be recycled to step a) in the form of a solution.

In a preferred process according to the invention, at least part of the second liquid phase obtained in step b) is recycled to step a). The second liquid phase in which the carboxylation catalyst is enriched, can be recycled to step a), e.g., into the carboxylation reactor.

The second liquid phase may be recycled to step a) with or without further workup steps. Further workup may include drying, i.e. the removal of water comprised by the second liquid phase and/or regenerating the alkoxide from the alcohol byproduct comprised by the second liquid phase by bringing the second liquid phase into contact with an alkaline material.

The distribution of the alcohol byproduct between the first and the second liquid phase does depend on the structure of the alcohol byproduct and on the exact composition of the first and of the second liquid phase obtained in step b).

Part of the alkoxide may therefore be regenerated from the alcohol byproduct comprised by the second liquid phase by bringing the second liquid phase into contact with an alkaline material as specified above, before the second liquid phase is recycled to step a). This is particularly advantageous when a relatively high proportion of the alcohol byproduct is present in the second liquid phase, in particular if 90% or more of the alcohol byproduct obtained in step a) is present in the second liquid phase obtained in step b).

Alternatively, the second liquid phase is recycled to step a) without regeneration of the alkoxide comprised by the second liquid phase. This alternative may, for example, be advantageous when at least 5% by weight of the alcohol byproduct, preferably at least 10% by weight of the alcohol byproduct, in particular at least 15% by weight of the alcohol byproduct, most preferably at least 20% by weight of the alcohol byproduct is comprised by the first liquid phase. This alternative is particularly advantageous when the polar solvent and the aprotic organic solvent are chosen such that the alcohol byproduct is enriched in the first liquid phase, e.g., if at least 50%, preferably at least 75% of the alcohol byproduct obtained in step a) is comprised by the first liquid phase obtained in step b).

In embodiments, wherein the alkoxide is regenerated by bringing the second liquid phase into contact with the alkaline material, the alkaline material can, for example, be added to the second liquid phase.

The invention will be described in more detail by the following examples.

In the examples, the following abbreviations are used:
Ni(COD)$_2$ Bis(1,5-cyclooctadiene)nickel(0)
THF tetrahydrofuran
TON turnover number with respect to transition metal

EXAMPLE 1

A 60 mL steel autoclave was charged inside a glovebox with Pd(PPh$_3$)$_4$ (0.22 mmol, 0.234 g), 1,2-bis(dicyclohexylphosphino)ethane (0.20 mmol, 0.093 g) and sodium tert-butoxide, (10 mmol, 1.1 g) in 30 mL of Anisole. The autoclave was removed from the glovebox and charged, under stirring at 800 rpm, with 10 bar of ethene and 20 bar of CO$_2$ (total pressure of 30 bar) for 15 min each at 25° C. After stirring for 20 hours at 145° C., the autoclave was cooled down to 20° C., the pressure was released and the reaction mixture, i.e. crude reaction product, was transferred into a 100 mL glass bottle. The residues in the autoclave vessel were recovered with 15 mL of D$_2$O and transferred in the glass bottle. In this biphasic mixture, 3-(trimethylsilyl) propionic-2,2,3,3-d$_4$ acid sodium salt (0.13 mmol, 0.0216 g) was added and an additional 10 mL of D$_2$O were added to the glass bottle. In order to favor the phase separation, 40 mL of Et$_2$O were added to the mixture. The organic phase, i.e. the second liquid phase contains the carboxylation catalyst and can be recycled. From the aqueous phase, i.e. the first liquid phase, an aliquot was collected, centrifuged and analyzed by $^1$H-NMR. A TON of 60 was determined by $^1$H-NMR (200 MHz, 70 scans). The $^1$H-NMR spectrum showed that the aqueous phase (=first liquid phase as described above) contains the α,β-ethylenically unsaturated carboxylic acid salt (sodium acrylate), the tertiary butanol byproduct and water. All volatiles were removed in vacuo from the aqueous phase to obtain the desired sodium acrylate as the residue. The residue was dissolved in D$_2$O and a second $^1$H-NMR spectrum was detected. The resonances of the methyl protons comprised by the tertiary butanol byproduct were not present in the second $^1$H-NMR spectrum, which shows that the tertiary butanol byproduct was quantitatively removed when the aqueous solvent was evaporated.

EXAMPLE 2

A 60 mL steel autoclave was charged inside a glovebox with Ni(COD)$_2$ (0.2 mmol, 0.056 g) (R,R)-(+)-1,2-Bis(di-t- butylmethylphosphino)benzene (0.22 mmol, 0.062 g) and sodium tert-butoxide, (10 mmol, 1.1 g) in 30 mL of THF. The autoclave was removed from the glovebox and charged, under stirring at 800 rpm, with 5 bar of ethene and 10 bar of $CO_2$ (total pressure of 15 bar) for 15 min each at 25° C. After stirring for 22 hours at 80° C., the autoclave was cooled down to 20° C., the pressure was released and the reaction mixture, i.e. the crude reaction product, was transferred into a 100 mL glass bottle. The residues in the autoclave vessel were recovered with 15 mL of $D_2O$ and transferred in the glass bottle. In this biphasic mixture, 3-(trimethylsilyl)propionic-2,2,3,3-$d_4$ acid sodium salt (0.13 mmol, 0.0216 g) was added and an additional 10 mL of $D_2O$ were added to the glass bottle. In order to favor the phase separation, 40 mL of $Et_2O$ were added to the mixture. From the aqueous phase, i.e. the first liquid phase, an aliquot was collected, centrifuged and analyzed by $^1$H-NMR. A TON of 14 was determined by $^1$H-NMR (200 MHz, 70 scans).

EXAMPLE 3

A 60 mL steel autoclave inside a glovebox was charged with $Ni(PPh_3)_4$ (0.22 mmol, 0.221 g), 1,2-bis(dicyclohexylphosphino)ethane (0.20 mmol, 0.0929 g), and sodium tert-butoxide, (10 mmol, 0.960 g) in 30 mL of Anisole. The autoclave was removed from the glovebox and charged under stirring at 800 rpm with 10 bar of ethene and 20 bar of $CO_2$ (total pressure of 30 bar) for 15 min each at 25° C. After stirring for 20 hours at 145° C. the autoclave was cooled down to 20° C., the pressure was released, and the reaction mixture, i.e. the crude reaction product, was transferred into a 100 mL glass bottle. The residues in the autoclave vessel were recovered with 15 mL of $D_2O$ and transferred in a glass bottle. To this biphasic mixture 3-(trimethylsilyl)propionic-2,2,3,3-$d_4$ acid sodium salt (0.13 mmol, 0.0216 g) was added, and additional 10 mL of $D_2O$ were added to the glass bottle. In order to favor the phase separation 40 mL of $Et_2O$ were added to the mixture. The organic phase, i.e. the second liquid phase, which contains the carboxylation catalyst can be recycled. From the aqueous phase, i.e. the first liquid phase, an aliquot was collected, centrifuged, and analyzed by $^1$H NMR. A TON of 10 was determined by $^1$H-NMR (200 MHz, 70 scans).

EXAMPLE 4

A 60 mL steel autoclave inside a glovebox was charged with $Pd(PPh_3)_4$ (0.22 mmol, 0.234 g), 1,2-bis(dicyclohexylphosphino)ethane (0.20 mmol, 0.0929 g), and sodium tert-butoxide, (20 mmol, 1.92 g) in 30 mL of Anisole. The autoclave was removed from the glovebox and charged under stirring at 800 rpm with 10 bar of ethene and 20 bar of $CO_2$ (total pressure of 30 bar) for 15 min each at 25° C. After stirring for 20 hours at 145° C. the autoclave was cooled down to 20° C., the pressure was released, and the reaction mixture, i.e. the crude reaction product, was transferred into a 100 mL glass bottle. The residues in the autoclave vessel were recovered with 15 mL of $D_2O$ and transferred in a glass bottle. To this biphasic mixture 3-(trimethylsilyl)propionic-2,2,3,3-$d_4$ acid sodium salt (0.13 mmol, 0.0216 g) was added, and additional 10 mL of $D_2O$ were added to the glass bottle. In order to favor the phase separation 40 mL of $Et_2O$ were added to the mixture. The organic phase, i.e. the second liquid phase, which contains the carboxylation catalyst can be recycled. From the aqueous phase, i.e. the first liquid phase, an aliquot was collected, centrifuged, and analyzed by $^1$H NMR. A TON of 88 was determined by $^1$H-NMR (200 MHz, 70 scans).

EXAMPLE 5

A 60 mL steel autoclave inside a glovebox was charged with $Pd(PPh_3)_4$ (0.22 mmol, 0.234 g), 1,2-bis(dicyclohexylphosphino)ethane (0.20 mmol, 0.0929 g), and sodium tert-butoxide, (11 mmol, 1.1 g) in 30 mL of anisole saturated with water. The autoclave was removed from the glovebox and charged under stirring at 800 rpm with 10 bar of ethene and 20 bar of $CO_2$ (total pressure of 30 bar) for 15 min each at 25° C. After stirring for 20 hours at 145° C. the autoclave was cooled down to 20° C., the pressure was released, and the reaction mixture, i.e. the crude reaction product, was transferred into a 100 mL glass bottle. The residues in the autoclave vessel were recovered with 15 mL of $D_2O$ and transferred in a glass bottle. To this biphasic mixture 3-(trimethylsilyl)propionic-2,2,3,3-$d_4$ acid sodium salt (0.13 mmol, 0.0216 g) was added, and additional 10 mL of $D_2O$ were added to the glass bottle. In order to favor the phase separation 40 mL of $Et_2O$ were added to the mixture. The organic phase, i.e. the second liquid phase, which contains the carboxylation catalyst can be recycled. From the aqueous phase, i.e. the first liquid phase, an aliquot was collected, centrifuged, and analyzed by $^1$H NMR. A TON of 56 was determined by $^1$H-NMR (200 MHz, 70 scans).

EXAMPLE 6

A 60 mL steel autoclave inside a glovebox was charged with $Pd(PPh_3)_4$ (0.01 mmol, 0.012 g), 1,2-bis(dicyclohexylphosphino)ethane (0.011 mmol, 0.005 g), and sodium tert-butoxide, (20 mmol, 0.960 g) in 30 mL of Anisole. The autoclave was removed from the glovebox and charged under stirring at 800 rpm with 10 bar of ethene and 20 bar of $CO_2$ (total pressure of 30 bar) for 15 min each at 25° C. After stirring for 65 hours at 145° C. the autoclave was cooled down to 20° C., the pressure was released, and the reaction mixture, i.e. the crude reaction product, was transferred into a 100 mL glass bottle. The residues in the autoclave vessel were recovered with 15 mL of $D_2O$ and transferred in a glass bottle. To this biphasic mixture 3-(trimethylsilyl)propionic-2,2,3,3-$d_4$ acid sodium salt (0.13 mmol, 0.0216 g) was added, and additional 10 mL of $D_2O$ were added to the glass bottle. In order to favor the phase separation 40 mL of $Et_2O$ were added to the mixture. The organic phase, i.e. the second liquid phase, which contains the carboxylation catalyst can be recycled. From the aqueous phase, i.e. the first liquid phase, an aliquot was collected, centrifuged, and analyzed by $^1$H NMR. A TON of 90 was determined by $^1$H-NMR (200 MHz, 70 scans).

EXAMPLE 7

A 60 mL steel autoclave inside a glovebox was charged with $Pd(PPh_3)_4$ (0.001 mmol, 0.001 g), 1,2-bis(dicyclohexylphosphino)ethane (0.0011 mmol, 0.001 g), and sodium tert-butoxide, (10 mmol, 0.960 g) in 30 mL of Anisole. The autoclave was removed from the glovebox and charged under stirring at 800 rpm with 10 bar of ethene and 20 bar of $CO_2$ (total pressure of 30 bar) for 15 min each at 25° C. After stirring for 65 hours at 145° C. the autoclave was cooled down to 20° C., the pressure was released, and the reaction mixture, i.e. the crude reaction product, was transferred into a 100 mL glass bottle. The residues in the autoclave vessel were recovered with 15 mL of $D_2O$ and transferred in a glass bottle. To this biphasic mixture 3-(trimethylsilyl)propionic-2,2,3,3-$d_4$ acid sodium salt (0.13 mmol, 0.0216 g) were added, and additional 10 mL of $D_2O$ were added to the glass bottle. In order to favor the phase separation 40 mL of $Et_2O$ were added to the mixture. The organic phase, i.e. the second liquid phase, which contains the carboxylation catalyst can be recycled. From the aqueous phase, i.e. the first liquid phase, an aliquot was collected, centrifuged, and analyzed by $^1H$ NMR. A TON of 100 was determined by $^1H$-NMR (200 MHz, 70 scans).

EXAMPLE 8

A 60 mL steel autoclave inside a glovebox was charged with $Pd(PPh_3)_4$ (0.2 mmol, 0.234 g), 1,2-bis(diisopropylphosphino)ethane (0.22 mmol, 0.058 g), and sodium tert-butoxide (10 mmol, 0.960 g) in 30 mL of Anisole. The autoclave was removed from the glovebox and charged under stirring at 800 rpm with 10 bar of ethene and 20 bar of $CO_2$ (total pressure of 30 bar) for 15 min each at 25° C. After stirring for 20 hours at 80° C. the autoclave was cooled down to 20° C., the pressure was released, and the reaction mixture, i.e. the crude reaction product, was transferred into a 100 mL glass bottle. The residues in the autoclave vessel were recovered with 15 mL of $D_2O$ and transferred in a glass bottle. To this biphasic mixture 3-(trimethylsilyl)propionic-2,2,3,3-$d_4$ acid sodium salt (0.13 mmol, 0.0216 g) was added, and additional 10 mL of $D_2O$ were added to the glass bottle. In order to favor the phase separation 40 mL of $Et_2O$ were added to the mixture. The organic phase, i.e. the second liquid phase, which contains the carboxylation catalyst can be recycled. From the aqueous phase, i.e. the first liquid phase, an aliquot was collected, centrifuged, and analyzed by $^1H$ NMR. A TON of 22 was determined by $^1H$-NMR (200 MHz, 70 scans).

EXAMPLE 9

A 60 mL steel autoclave inside a glovebox was charged with $Pd(PPh_3)_4$ (0.2 mmol, 0.234 g), 1,2-bis(didodecenyl-phosphino)ethane (0.22 mmol, 0.193 g), and sodium tert-butoxide, (10 mmol, 0.960 g) in 30 mL of Anisole. The autoclave was removed from the glovebox and charged under stirring at 800 rpm with 10 bar of ethene and 20 bar of $CO_2$ (total pressure of 30 bar) for 15 min each at 25° C. After stirring for 20 hours at 80° C. the autoclave was cooled down to 20° C., the pressure was released, and the reaction mixture, i.e. the crude reaction product, was transferred into a 100 mL glass bottle. The residues in the autoclave vessel were recovered with 15 mL of $D_2O$ and transferred in a glass bottle. To this biphasic mixture 3-(trimethylsilyl)propionic-2,2,3,3-$d_4$ acid sodium salt (0.13 mmol, 0.0216 g) was added, and additional 10 mL of $D_2O$ were added to the glass bottle. In order to favor the phase separation 40 mL of $Et_2O$ were added to the mixture. The organic phase, i.e. the second liquid phase, which contains the carboxylation catalyst can be recycled. From the aqueous phase, i.e. the first liquid phase, an aliquot was collected, centrifuged, and analyzed by $^1H$ NMR. A TON of 10 was determined by $^1H$-NMR (200 MHz, 70 scans).

EXAMPLE 10

A 60 mL steel autoclave inside a glovebox was charged with $Pd(PPh_3)_4$ (0.2 mmol, 0.234 g), 1,2-bis(ditertbutyl-phosphino)ethane (0.22 mmol, 0.142 g), and sodium tert-butoxide, (10 mmol, 0.960 g) in 30 mL of Anisole. The autoclave was removed from the glovebox and charged under stirring at 800 rpm with 10 bar of ethene and 20 bar of $CO_2$ (total pressure of 30 bar) for 15 min each at 25° C. After stirring for 20 hours at 80° C. the autoclave was cooled down to 20° C., the pressure was released, and the reaction mixture, i.e. the crude reaction product, was transferred into a 100 mL glass bottle. The residues in the autoclave vessel were recovered with 15 mL of $D_2O$ and transferred in a glass bottle. To this biphasic mixture 3-(trimethylsilyl)propionic-2,2,3,3-$d_4$ acid sodium salt (0.13 mmol, 0.0216 g) was added, and additional 10 mL of $D_2O$ were added to the glass bottle. In order to favor the phase separation 40 mL of $Et_2O$ were added to the mixture. The organic phase, i.e. the second liquid phase, which contains the carboxylation catalyst can be recycled. From the aqueous phase, i.e. the first liquid phase, an aliquot was collected, centrifuged, and analyzed by $^1H$ NMR. A TON of 3 was determined by $^1H$-NMR (200 MHz, 70 scans).

EXAMPLE 11

A 60 mL steel autoclave inside a glovebox was charged with $Pd(PPh_3)_4$ (0.2 mmol, 0.234 g), 1,2-bis(dicyclopentylphosphino)ethane bistetrafluoroborate (0.22 mmol, 0.120 g), and sodium tert-butoxide, (10 mmol, 0.960 g) in 30 mL of Anisole. The autoclave was removed from the glovebox and charged under stirring at 800 rpm with 10 bar of ethene and 20 bar of $CO_2$ (total pressure of 30 bar) for 15 min each at 25° C. After stirring for 20 hours at 80° C. the autoclave was cooled down to 20° C., the pressure was released, and the reaction mixture, i.e. the crude reaction product, was transferred into a 100 mL glass bottle. The residues in the autoclave vessel were recovered with 15 mL of $D_2O$ and transferred in a glass bottle. To this biphasic mixture 3-(trimethylsilyl)propionic-2,2,3,3-$d_4$ acid sodium salt (0.13 mmol, 0.0216 g) was added, and additional 10 mL of $D_2O$ were added to the glass bottle. In order to favor the phase separation 40 mL of $Et_2O$ were added to the mixture. The organic phase, i.e. the second liquid phase, which contains the carboxylation catalyst can be recycled. From the aqueous phase, i.e. the first liquid phase, an aliquot was collected, centrifuged, and analyzed by $^1H$ NMR. A TON of 5 was determined by $^1H$-NMR (200 MHz, 70 scans).

EXAMPLE 12

A 60 mL steel autoclave inside a glovebox was charged with $Pd(PPh_3)_4$ (0.22 mmol, 0.234 g), 1,2-bis(dicyclohexylphosphino)ethane (0.20 mmol, 0.0929 g), sodium tert-butoxide, (11 mmol, 1.1 g), and 1,3-butadiene (1.5M in Toluene, 10 mL) in 30 mL of Anisole. The autoclave was removed from the glovebox and charged under stirring at 800 rpm with 20 bar of $CO_2$ for 15 min at 25° C. After stirring for 3 hours at 100° C. the autoclave was cooled down to 20° C., the pressure was released, and the reaction mixture, i.e. the crude reaction product, was transferred into a 100 mL glass bottle. The residues in the autoclave vessel were recovered with 15 mL of $D_2O$ and transferred in a glass bottle. To this biphasic mixture 3-(trimethylsilyl)propionic-2,2,3,3-$d_4$ acid sodium salt (0.13 mmol, 0.0216 g) were added, and additional 10 mL of $D_2O$ were added to the glass bottle. In order to favor the phase separation 40 mL of $Et_2O$ were added to the mixture. The organic phase, i.e. the second liquid phase, which contains the carboxylation catalyst can be recycled. From the aqueous phase, i.e. the first liquid phase, an aliquot was collected, centrifuged, and analyzed by $^1$H NMR. A TON of 60 was determined by $^1$H-NMR (200 MHz, 70 scans).

EXAMPLE 13

A 60 mL steel autoclave inside a glovebox was charged with $Pd(PPh_3)_4$ (0.22 mmol, 0.234 g), 1,2-bis(dicyclohexylphosphino)ethane (0.20 mmol, 0.0929 g), sodium tert-butoxide, (11 mmol, 1.1 g), and 1-hexene (30 mmol, 3.8 mL) in 30 mL of Anisole. The autoclave was removed from the glovebox and charged under stirring at 800 rpm with 20 bar of $CO_2$ for 15 min at 25° C. After stirring for 3 hours at 100° C. the autoclave was cooled down to 20° C., the pressure was released, and the reaction mixture, i.e. the crude reaction product, was transferred into a 100 mL glass bottle. The residues in the autoclave vessel were recovered with 15 mL of $D_2O$ and transferred in a glass bottle. To this biphasic mixture 3-(trimethylsilyl)propionic-2,2,3,3-$d_4$ acid sodium salt (0.13 mmol, 0.0216 g) was added, and additional 10 mL of $D_2O$ were added to the glass bottle. In order to favor the phase separation 40 mL of $Et_2O$ were added to the mixture.

The organic phase, i.e. the second liquid phase, which contains the carboxylation catalyst can be recycled. From the aqueous phase, i.e. the first liquid phase, an aliquot was collected, centrifuged, and analyzed by $^1$H NMR. A TON of 13 (3.3 n/i and 2.3 E/Z ratio) was determined by $^1$H-NMR (200 MHz, 70 scans).

EXAMPLE 14

A 60 mL steel autoclave inside a glovebox was charged with $Pd(PPh_3)_4$ (0.22 mmol, 0.234 g), 1,2-bis(dicyclohexylphosphino)ethane (0.20 mmol, 0.0929 g), sodium tert-butoxide, (11 mmol, 1.1 g) in 30 mL of Anisole. The autoclave was removed from the glovebox and charged without stirring with 7 bar of propylene for 3 min and under stirring at 800 rpm with 20 bar of $CO_2$ for 15 min at 25° C. After stirring for 3 hours at 100° C. the autoclave was cooled down to 20° C., the pressure was released, and the reaction mixture, i.e. the crude reaction product, was transferred into a 100 mL glass bottle. The residues in the autoclave vessel were recovered with 15 mL of $D_2O$ and transferred in a glass bottle. To this biphasic mixture 3-(trimethylsilyl)propionic-2,2,3,3-$d_4$ acid sodium salt (0.13 mmol, 0.0216 g) were added, and additional 10 mL of $D_2O$ were added to the glass bottle. In order to favor the phase separation 40 mL of $Et_2O$ were added to the mixture. The organic phase, i.e. the second liquid phase, which contains the carboxylation catalyst can be recycled. From the aqueous phase, i.e. the first liquid phase, an aliquot was collected, centrifuged, and analyzed by $^1$H NMR. A TON of 16 (1.7 n/i and 2.0 E/Z ratio) was determined by $^1$H-NMR (200 MHz, 70 scans).

EXAMPLE 15

A 60 mL steel autoclave inside a glovebox was charged with $Pd(PPh_3)_4$ (0.22 mmol, 0.234 g), 1,2-bis(dicyclohexylphosphino)ethane (0.20 mmol, 0.0929 g), sodium tert-butoxide, (11 mmol, 1.1 g), and styrene (30 mmol, 3.5 mL) in 30 mL of Anisole. The autoclave was removed from the glovebox and charged under stirring at 800 rpm with 20 bar of $CO_2$ for 15 min at 25° C. After stirring for 3 hours at 100° C. the autoclave was cooled down to 20° C., the pressure was released, and the reaction mixture, i.e. the crude reaction product, was transferred into a 100 mL glass bottle. The residues in the autoclave vessel were recovered with 15 mL of $D_2O$ and transferred in a glass bottle. To this biphasic mixture 3-(trimethylsilyl)propionic-2,2,3,3-$d_4$ acid sodium salt (0.13 mmol, 0.0216 g) was added, and additional 10 mL of $D_2O$ were added to the glass bottle. In order to favor the phase separation 40 mL of $Et_2O$ were added to the mixture. The organic phase, i.e. the second liquid phase, which contains the carboxylation catalyst can be recycled. From the aqueous phase, i.e. the first liquid phase, an aliquot was collected, centrifuged, and analyzed by $^1$H NMR. A TON of 5 was determined by
$^1$H-NMR (200 MHz, 70 scans).

EXAMPLE 16

A 60 mL steel autoclave inside a glovebox was charged with $Pd(PPh_3)_4$ (0.22 mmol, 0.234 g), 1,2-bis(dicyclohexylphosphino)ethane (0.20 mmol, 0.0929 g), sodium tert-butoxide, (11 mmol, 1.1 g), and cyclopentene (30 mmol, 2.7 mL) in 30 mL of Anisole. The autoclave was removed from the glovebox and charged under stirring at 800 rpm with 20 bar of $CO_2$ for 15 min at 25° C. After stirring for 3 hours at 100° C. the autoclave was cooled down to 20° C., the pressure was released, and the reaction mixture, i.e. the crude reaction product, was transferred into a 100 mL glass bottle. The residues in the autoclave vessel were recovered with 15 mL of $D_2O$ and transferred in a glass bottle. To this biphasic mixture, 3-(trimethylsilyl)propionic-2,2,3,3-$d_4$ acid sodium salt (0.13 mmol, 0.0216 g) were added, and additional 10 mL of $D_2O$ were added to the glass bottle. In order to favor the phase separation 40 mL of $Et_2O$ were added to the mixture. The organic phase, i.e. the second liquid phase, which contains the carboxylation catalyst can be recycled. From the aqueous phase, i.e. the first liquid phase, an aliquot was collected, centrifuged, and analyzed by $^1$H NMR. A TON of 6 was determined by $^1$H-NMR (200 MHz, 70 scans).

EXAMPLE 17

A 60 mL steel autoclave inside a glovebox was charged with $(Pd(PPh_3)_4$ (0.22 mmol, 0.234 g), 1,2-bis(dicyclohexylphosphino)ethane (0.20 mmol, 0.0929 g) and sodium tert-butoxide, (10 mmol, 960 mg). The solid mixture was dissolved in 30 mL of anisole. The autoclave was removed from the glovebox and charged under stirring at 800 rpm with 10 bar of ethene and 20 bar of $CO_2$ (total pressure 30 bar) for 15 min each at 25° C. After stirring at 145° C. and for 20 hours at 800 rpm the autoclave was cooled to 20° C., the pressure was released, and the autoclave was re-introduced in the glovebox. The reaction mixture, i.e. the crude reaction product, was transferred into a 100 ml Schlenk flask equipped with a magnetic bar. Outside the glovebox 30 mL of degassed water were added through a syringe. The mixture was stirred for 10 min at room temperature in order to favor the dissolution of sodium acrylate and let the two phase settle for 2 minutes. The water phase was analyzed as described in the other examples achieving a TON of 60. The organic phase was re-introduced in the glovebox, filtered through a microfilter, and transferred in a 60 mL steel autoclave previously charged with sodium tert-butoxide, (10 mmol, 0.960 g), and Zn (1 mmol). The autoclave was then removed from the glovebox and charged under stirring at 800 rpm with 10 bar of ethene and 20 bar of $CO_2$ (total pressure 30 bar) for 15 min each at 25° C. After stirring at 145° C. for another 20 hours at 800 rpm, the reaction was purified and analyzed as previously described achieving a TON of 25.

EXAMPLE 18

A 60 mL steel autoclave inside a glovebox was charged with $(Pd(PPh_3)_4$ (0.22 mmol, 0.234 g), 1,2-bis(dicyclohexylphosphino)ethane (0.20 mmol, 0.0929 g), and sodium tert-butoxide, (10 mmol, 960 mg). The solid mixture was dissolved in 30 mL of anisole. The autoclave was removed from the glovebox and charged under stirring at 800 rpm with 10 bar of ethene and 20 bar of $CO_2$ (total pressure 30 bar) for 15 min each at 25° C. After stirring at 145° C. and for 20 hours at 800 rpm the autoclave was cooled to 20° C., the pressure was released, and the autoclave was re-introduced in the glovebox. The reaction mixture, i.e. the crude reaction product, was transferred into a 100 ml Schlenk flask equipped with a magnetic bar. Outside the glovebox 30 mL of degassed water were added through a syringe. The mixture was stirred for 10 min at room temperature in order to favor the dissolution of sodium acrylate and let the two phase settle for 2 minutes. The water phase was analyzed as described in the other examples achieving a TON of 60. The organic phase was re-introduced in the glovebox and transferred in a 60 mL steel autoclave previously charged with Zn (1 mmol). Outside the glovebox the autoclave was pressurized with 20 bar of $C_2H_4$ and left to stir at 800 rpm for 1.5 h. At time elapsed the pressure was released and the autoclave was re-introduced inside the glovebox. The solid mixture was filtered and transferred in a 60 mL steel autoclave previously charged with sodium tert-butoxide, (10 mmol, 0.960 g).

Outside the glovebox the autoclave was pressurized with 10 bar of ethene and 20 bar of $CO_2$ (total pressure 30 bar) for 15 min each at 25° C. After stirring at 145° C. for another 20 hours at 800 rpm, the reaction was purified and analyzed as previously described achieving a TON of 18.

EXAMPLE 19

A 60 mL steel autoclave inside a glovebox was charged with $(Pd(PPh_3)_4$ (0.22 mmol, 0.234 g), 1,2-bis(dicyclohexylphosphino)ethane (0.20 mmol, 0.0929 g), and sodium tert-butoxide, (10 mmol, 960 mg). The solid mixture was dissolved in 30 mL of anisole. The autoclave was removed from the glovebox and charged under stirring at 800 rpm with 10 bar of ethene and 20 bar of $CO_2$ (total pressure 30 bar) for 15 min each at 25° C. After stirring at 145° C. and for 20 hours at 800 rpm the autoclave was cooled to 20° C., the pressure was released, and the autoclave was re-introduced in the glovebox. The reaction mixture, i.e. the crude reaction product, was transferred into a 100 ml Schlenk flask equipped with a magnetic bar. Outside the glovebox 30 mL of degassed water were added through a syringe. The mixture was stirred for 10 min at room temperature in order to favor the dissolution of sodium acrylate and let the two phase settle for 2 minutes. The water phase was analyzed as described in the other examples achieving a TON of 60. The organic phase was re-introduced in the glovebox, transferred in a 60 mL steel autoclave. Outside the glovebox the autoclave was pressurized with 30 bar of $C_2H_4$ and left to stir at 800 rpm for 1.5 h. At time elapsed the pressure was released and the autoclave was re-introduced inside the glovebox. The solid mixture was filtered and transferred in a 60 mL steel autoclave previously charged with sodium tert-butoxide, (10 mmol, 0.960 g). Outside the glovebox the autoclave was pressurized with 10 bar of ethene and 20 bar of $CO_2$ (total pressure 30 bar) for 15 min each at 25° C. After stirring at 145° C. for another 20 hours at 800 rpm, the reaction was purified and analyzed as previously described achieving a TON of 18.

EXAMPLE 20

A 60 mL steel autoclave inside a glovebox was charged with $(Pd(PPh_3)_4$ (0.22 mmol, 0.234 g), 1,2-bis(dicyclohexylphosphino)ethane (0.20 mmol, 0.0929 g), and sodium tert-butoxide, (10 mmol, 960 mg). The solid mixture was dissolved in 30 mL of anisole. The autoclave was removed from the glovebox and charged under stirring at 800 rpm with 10 bar of ethene and 20 bar of $CO_2$ (total pressure 30 bar) for 15 min each at 25° C. After stirring at 145° C. and for 20 hours at 800 rpm the autoclave was cooled to 20° C., the pressure was released, and the autoclave was re-introduced in the glovebox. The reaction mixture, i.e. the crude reaction product, was transferred into a 100 ml Schlenk flask equipped with a magnetic bar. Outside the glovebox 30 mL of degassed water were added through a syringe. The mixture was stirred for 10 min at room temperature in order to favor the dissolution of sodium acrylate and let the two phase settle for 2 minutes. The water phase was analyzed as described in the other examples achieving a TON of 60. The organic phase was re-introduced in the glovebox. The solid mixture was filtered and transferred in a 60 mL steel autoclave previously charged with sodium tert-butoxide, (10 mmol, 0.960 g). Outside the glovebox the autoclave was pressurized with 10 bar of ethene and 20 bar of $CO_2$ (total pressure 30 bar) for 15 min each at 25° C. After stirring at 145° C. for another 20 hours at 800 rpm the reaction was purified and analyzed as previously described achieving a TON of 15.

The results show that an efficient catalytic preparation of $\alpha,\beta$-ethylenically unsaturated carboxylic acid derivatives from $CO_2$ and an alkene is achieved in the process of the invention and that the $\alpha,\beta$-ethylenically unsaturated carboxylic acid salt can easily be separated from the catalyst and the alcohol byproduct. The results also show that the second liquid phase comprising the carboxylation catalyst can be recycled into the carboxylation reaction.

The invention claimed is:

1. A catalytic process for preparing an $\alpha, \beta$-ethylenically unsaturated carboxylic acid salt, the process comprising:
   a) contacting an alkene and carbon dioxide with a carboxylation catalyst and an alkoxide, the alkoxide having a secondary or tertiary carbon atom directly bound to a [O⁻] group, to obtain a crude reaction product comprising the $\alpha,\beta$-ethylenically unsaturated carboxylic acid salt and an alcohol byproduct which is a conjugate acid of the alkoxide,
   b) contacting at least part of the crude reaction product with a polar solvent such that a first liquid phase in which the $\alpha,\beta$-ethylenically unsaturated carboxylic acid salt is enriched, and a second liquid phase in which the carboxylation catalyst is enriched, are obtained, and
   c) distilling an alcohol byproduct off from the first liquid phase.

2. The catalytic process according to claim 1, further comprising:
   d) contacting at least part of the alcohol byproduct recovered in c) with an alkaline material in order to regenerate the alkoxide.

3. The catalytic process according to claim 2, wherein at least part of the alkoxide obtained in d) is recycled to a).

4. The catalytic process according to claim 1, wherein at least part of the second liquid phase obtained in b) is recycled to a).

5. The catalytic process according to claim 1, wherein the polar solvent has a boiling temperature of less than 150° C. at a pressure of 1 bar.

6. The catalytic process according to claim 1, wherein the polar solvent comprises at least 90% by weight of water.

7. The catalytic process according to claim 5, wherein, in c), at least a part of the polar solvent is distilled off from the first liquid phase.

8. The catalytic process according to claim 7, wherein the polar solvent recovered in c) is used as the polar solvent in b).

9. The catalytic process according to claim 1, wherein a) is carried out in an aprotic organic solvent.

10. The catalytic process according to claim 9, wherein the aprotic organic solvent is octane, nonane, decane, undecane, dodecane, tridecane, tetradecane, pentadecane, hexadecane, heptadecane, octadecane, benzene, toluene, xylene, chlorobenzene, anisole, butyl-phenyl-ether, diphenylether, dibutylether, ethylenglcyoledibutlyether, diethylether, tetrahydrofuran, 2-methyl-tetrahydrofuran, or a mixture thereof.

11. The catalytic process according to claim 1, wherein the partial pressure of carbon dioxide in a) is maintained above 1 bar.

12. The catalytic process according to claim 1, wherein the alkoxide is selected from the group consisting of an alkali metal alkoxide and an alkaline earth metal alkoxide.

13. The catalytic process according to claim 1, wherein the alkoxide is sodium tert-butoxide.

14. The catalytic process according to claim 1, wherein a) is carried out at a temperature ranging from 70 to 180° C.

15. The catalytic process according to claim 1, wherein the carboxylation catalyst is a nickel or palladium complex which comprises a bidentate P,X ligand in which X is selected from the group consisting of P, N O, and carbene, and the P and X atom is separated by a bivalent linker that comprises 2 to 4 bridging atoms.

16. The catalytic process according to claim 15, wherein the P,X ligand is a P,P ligand of formula (IId-1)

$$R^{16}R^{17}P-(CR^{18}H)_e-PR^{16}R^{17} \qquad \text{(IId-1)}$$

wherein $R^{16}$ and $R^{17}$ are each independently an unbranched or branched, acyclic or cyclic aliphatic residue having 1 to 20 carbon atoms, e is 2, 3, or 4, and $R^{18}$ is independently H, $C_1$-$C_8$-alkyl, $C_1$-$C_8$-alkoxy, $C_3$-$C_{10}$-cycloalkyl, $C_3$-$C_{10}$-cycloalkoxy, $C_6$-$C_{10}$-aryl, or $C_6$-$C_{10}$-aryloxy.

17. The catalytic process according to claim 1, wherein the alkene is ethene and the α,β-ethylenically unsaturated carboxylic acid is acrylic acid.

* * * * *

UNITED STATES PATENT AND TRADEMARK OFFICE
CERTIFICATE OF CORRECTION

PATENT NO. : 10,138,196 B2
APPLICATION NO. : 15/573276
DATED : November 27, 2018
INVENTOR(S) : Thomas Schaub et al.

It is certified that error appears in the above-identified patent and that said Letters Patent is hereby corrected as shown below:

On the Title Page

Column 2, item (57), In the Abstract, Line 6, "β,β-ethylenically" should read --α,β-ethylenically--.

In the Specification

Column 4, Line 61, "cyclohexl))." should read --cyclohexyl)).--.

Column 8, Line 21, "$R_{15}$" should read --$R^{15}$--;
　　　　Line 51, "non-interfereing" should read --non-interfering--.

Column 12, Line 14, "$[Pd(C_6H^5CN)_2(Cl)_2]$," should read --$[Pd(C_6H_5CN)_2(Cl)_2]$,--.

Column 14, Line 12, "10.1002114356007.b04_087" should read
--10.1002/114356007.b04_087--.

Column 18, Line 54, "$C_6$-$C_{10}$-aryl," should read --$C_{6-10}$-aryl,--.

In the Claims

Column 30, Line 8, Claim 15, "P,N O," should read --P,N,O,--.

Signed and Sealed this
Twelfth Day of November, 2019

Andrei Iancu
*Director of the United States Patent and Trademark Office*